(12) United States Patent
Rapp et al.

(10) Patent No.: US 6,689,560 B1
(45) Date of Patent: *Feb. 10, 2004

(54) RAF PROTEIN KINASE THERAPEUTICS

(75) Inventors: Ulf R. Rapp, Washington, DC (US);
Harald App, Frederick, MD (US);
Stephen M. Storm, Frederick, MD (US)

(73) Assignee: The United States of America as represented by the Department of Health and Human Services, Washington, DC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/207,954

(22) Filed: Mar. 18, 1994

Related U.S. Application Data

(63) Continuation of application No. 07/748,931, filed on Aug. 23, 1991, now abandoned.

(51) Int. Cl.[7] ............................. C12Q 1/68; C12Q 1/02; C12N 15/85
(52) U.S. Cl. ................................ 435/6; 435/4; 435/29; 435/375; 435/455; 536/24.5
(58) Field of Search ................................ 435/6, 5, 375, 435/4, 29, 455; 514/44; 536/24.5

(56) References Cited

U.S. PATENT DOCUMENTS 4,740,463 A  4/1988 Weinberg et al. ........... 435/456

OTHER PUBLICATIONS

Orkin et al., "Report and Recommendations of the panel to assess the NIH invesment in research on gene therapy", issued by the National Institutes of Health, Dec. 1995.*
Ellis et al. (1990) "Phosphorylation of GAP and GAP–Associated Proteins by Transforming and Nitrogenic Tyrosine Kinases" Nature 343: 377–381.*
Cantley et al. (1991) "Oncogenes and Signal Transduction." Cell 64: 281–302.*
Hunter et al. (1991) "Cooperation Between Oncogenes" Cell 64: 249–270.*
Ishikawa et al (1988) Identification of a Transforming Activity Suppressing Sequence in the C–Raf Cocogene 3 (6): 653–658.*
Soderling (1990) Protein Kinases: Regulation by Antoinhibitory Domains. J. Biol. Chem. 265 (4): 1823–1826.*
Heidecker et al. (1990) Mutational activation of C–Raf–1 and Definition of the Minimal Transforming Sequence. Mol. Cell. Biol. 10(6): 2503–2512.*
Feig et al. (1988) Inhibition of NIH 3T3 Cell Proliferation by a Mutant Raf Protein . . . Mol. Cell. Biol. 8(8): 3235–3243.*
App et al. "Epidermal Growth Factor (EGF) Stimulates Association and Kinase Activity of Raf–1 with the EGF Receptor" Mol. and Cell. Biol. 11(2):913–919, Feb. 1991.
Kolch et al. "Raf–1 protein kinase is required for growth of induced NIH/3T3 cells" Nature 349:426–428, Jan. 31, 1991.
Rapp et al. "Oncogenes: Clinical Relevance" *Haematol. and Blood Transf.* 31:450–459, 1987(a).
Rapp et al. "Transformation by *raf* and *myc* Oncogenes" in *Oncogenes and Cancer*, Ed. Aaronson et al., pp. 55–74, 1987(b).
Bonner et al. "The Complete Coding Sequence of the Human *raf* Oncogene and the Corresponding Structure of the c–*raf*–1 gene" *Nucl. Acids Res.* 14(2):1009–1015, 1986.

* cited by examiner

*Primary Examiner*—Scott D. Priebe
(74) *Attorney, Agent, or Firm*—Needle & Rosenberg, P.C.

(57) ABSTRACT

It is a general object of this invention to provide a DNA segment comprising a Raf gene in an antisense orientation downstream of a promoter. It is a specific object of this invention to provide a method of inhibiting Raf expression comprising expressing an antisense Raf gene in a cell such that said Raf expression is inhibited. It is a further object of the invention to provide a method of inhibiting Raf kinase activity comprising replacement of a serine or threonine amino acid within the Raf gene for a non-phosphorylated amino acid.

11 Claims, 20 Drawing Sheets

F12/pMNC 301

Figure 1:
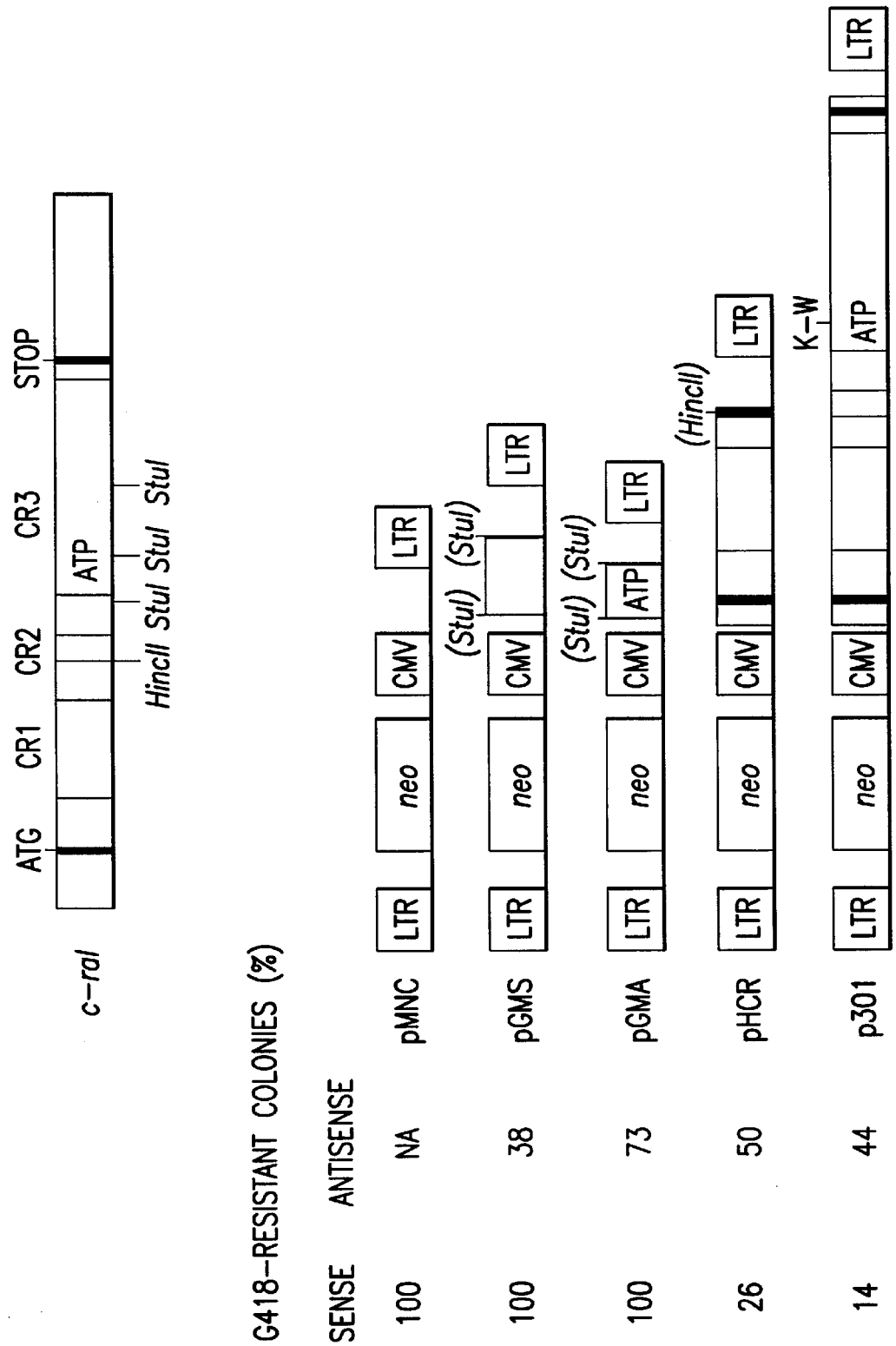

| | Flat | Intermediate | Transformed |
|---|---|---|---|
| pMNC | 1% | 4% | 95% |
| pMNC 301-1 | 25% | 22% | 53% |
| pMNC 301-2 | 10% | 28% | 62% |

FIG.2A

F4/GMS

| | Flat | Intermediate | Transformed |
|---|---|---|---|
| pMNC | 0% | 3% | 97% |
| pGMS-8 | 9% | 35% | 56% |
| pGMS-7 | 0% | 2% | 98% |

FIG.2B

```
CCG AAT GTG ACC GCC TCC CTC ACC CGC TCC CTC CGC GGG GAG GAG GAG CGG GCG AGA AGC TGC CGC CGA ACG ACA GGA CGT TGG GGC GGC CTG GCT CCC    99
Exon 2

TCA GGT TTA AGA ATT GTT TAA GCT GCA TCA ATG GAG CAC ATA CAG GGA GCT TGG AAG ACG ATC AGC AAT GGT TTT GGA TTC AAA GAT GCC GTG TTT GAT   198
                          Met Glu His Ile Gln Gly Ala Trp Lys Thr Ile Ser Asn Gly Phe Gly Phe Lys Asp Ala Val Phe Asp

GGC TCC AGC TGC ATC TCT CCT ACA ATA GTT CAG CAG TTT GGC TAT CAG CGC CGG GCA TCA GAT GAT GGC AAA CTC ACA GAT CCT TCT AAG ACA AGC AAC   297
Gly Ser Ser Cys Ile Ser Pro Thr Ile Val Gln Gln Phe Gly Tyr Gln Arg Arg Ala Ser Asp Asp Gly Lys Leu Thr Asp Pro Ser Lys Thr Ser Asn
                                                                             Exon 3

ACT ATC CGT GTT TTC TTG CCG AAC AAG CAA AGA ACA GTG GTC AAT GGA ATG AGC TTG CAT GAC TGC CTT ATG AAA GCA CTC AAG GTG AGG   396
Thr Ile Arg Val Phe Leu Pro Asn Lys Gln Arg Thr Val Val Asn Gly Met Ser Leu His Asp Cys Leu Met Lys Ala Leu Lys Val Arg

GGC CTG CAA CCA GAG TGC TGT GCA GTG TTC AGA CTT CTC CAC GAA CTT CTA GAT TGG AAT ACT GCT GCG TCT TTG ATT   495
Gly Leu Gln Pro Glu Cys Cys Ala Val Phe Arg Leu Leu His Glu Leu Leu Asp Trp Asn Thr Ala Ala Ser Leu Ile
                                                                                                   Exon 5

GGA GAA GAA CTT CAA GTA GAT TTC CTG AAT GGA TTT CGA TGT CAG ACT TGT GGC TAC AAA TTT CAT GAG CAC TGT AGC ACC AAA GTA CCT ACT ATG TGT GTG GAC TGG AGT   594
Gly Glu Glu Leu Gln Val Asp Phe Leu Asn Gly Phe Arg Cys Gln Thr Cys Gly Tyr Lys Phe His Glu His Cys Ser Thr Lys Val Pro Thr Met Cys Val Asp Trp Ser

CAG AAA TTC CTG CTC AAT GGA TTT CGA TGT CAG ACT TGT GGC TAC AAA TTT CAT GAG CAC TGT AGC ACC AAA GTA CCT ACT ATG TGT GTG GAC TGG AGT   693
Gln Lys Phe Leu Leu Asn Gly Phe Arg Cys Gln Thr Cys Gly Tyr Lys Phe His Glu His Cys Ser Thr Lys Val Pro Thr Met Cys Val Asp Trp Ser
Exon 6

AAC ATC AGA CAA CTC TTA TTG TTT CCA AAT CCC ACT ATT GGT GAT AGT GGA GTC CCA GCA CTA CCT TTG ACT ATG CGT ATG CGA GAG TCT GTT   792
Asn Ile Arg Gln Leu Leu Leu Phe Pro Asn Pro Thr Ile Gly Asp Ser Gly Val Pro Ala Leu Pro Leu Thr Met Arg Met Arg Glu Ser Val
```

FIG.9A

```
Exon 7
                                                                                                            891
TCC AGG ATG CCT GTT TCT CAG CAC AGA TAT TCT ACA CCT CAC GCC TTC ACC AGT CCC TCA TCT GAA GGT TCC CTC CAG AGG
Ser Arg Met Pro Val Ser Ser Gln His Arg Tyr Ser Thr Pro His Ala Phe Thr Ser Pro Ser Ser Glu Gly Ser Leu Gln Arg
                                                                                                     Exon 8
                                                                                                            990
CAG AGG TCG ACA TCC ACA CCT AAT GTC CAC ATG AGC GTC ACC ACG CTG CCT GTG GAC AGC AGG ATG ATT GAG GAT GCA ATT CGA AGT CAC AGC GAA TCA
Gln Arg Ser Thr Ser Thr Pro Asn Val His Met Ser Val Thr Thr Leu Pro Val Asp Ser Arg Met Ile Glu Asp Ala Ile Arg Ser His Ser Glu Ser
Exon 9
                                                                                                            1089
GCC TCA CCT TCA GCC CTG TCC AGT AGC CCC AAC AAT CTG AGC CCA ACA GGC TGG TCA CAG CCG AAA ACC CCC GTG CCA GCA CAA AGA GAG CGG GCA CCA
Ala Ser Pro Ser Ala Leu Ser Ser Ser Pro Asn Asn Leu Ser Pro Thr Gly Trp Ser Gln Pro Lys Thr Pro Val Pro Ala Gln Arg Glu Arg Ala Pro
                                                                                      Exon 10
                                                                                                            1188
GTA TCT GGG ACC CAG GAG AAA AAC ATT AGG CCT CGT GGA CAG AGA TCA AGC TAT TAT TGG GAA ATA GAA GCC AGT GAA GTG ATG CTG TCC ACT
Val Ser Gly Thr Gln Glu Lys Asn Ile Arg Pro Arg Gly Gln Arg Ser Ser Tyr Tyr Trp Glu Ile Glu Ala Ser Glu Val Met Leu Ser Thr
                                                                                Exon 11
                                                                                                            1287
CGG ATT GGG TCA GGC TCT TTT GGA ACT GTT TAT AAG GGT GTT GCA GGA GAT GTT GCA GTA AAG ATC CTA AAG ATT GTC GAC CCA ACC CCA GAG CAA
Arg Ile Gly Ser Gly Ser Phe Gly Thr Val Tyr Lys Gly Val Ala Gly Asp Val Ala Val Lys Ile Leu Lys Ile Val Asp Pro Thr Pro Glu Gln
                                                                                                            1386
TTC CAG GCC TTC AGG AAT GAG GTG GCT GTT CTG CGC AAA ACA CGG CAT GTG AAC ATT CTG CTT TTC ATG GGG TAC ATG AAG GAC AAC CTG GCA ATT
Phe Gln Ala Phe Arg Asn Glu Val Ala Val Leu Arg Lys Thr Arg His Val Asn Ile Leu Leu Phe Met Gly Tyr Met Lys Asp Asn Leu Ala Ile
                                                                                Exon 12
                                                                                                            1485
GTG ACC CAG TGG TGC GAG GGC AGC AGC CTC TAC AAA CAC CTG CAT GTC CAG GAG ACC AAG TTT CAG ATG TTC CAG CTA ATT GAC ATT GCC CGG CAG ACG
Val Thr Gln Trp Cys Glu Gly Ser Ser Leu Tyr Lys His Leu His Val Gln Glu Thr Lys Phe Gln Met Phe Gln Leu Ile Asp Ile Ala Arg Gln Thr
Exon 13                                                                                    Exon 14
                                                                                                            1584
GCT CAG GGA GAC TAT TTG CAT GCA AAG AAC ATC CAT AGA GAC ATG AAA TCC AAC AAT ATA TTT CTC CAT GAA GGC TTA ACA GTG AAA ATT GGA
Ala Gln Gly Asp Tyr Leu His Ala Lys Asn Ile His Arg Asp Met Lys Ser Asn Asn Ile Phe Leu His Glu Gly Leu Thr Val Lys Ile Gly
```

FIG.9B

```
                                                                                                    Exon 15
                                                                                                    |    1683
GAT TTT GGT TTG GCA ACA GTA AAG TCA CGC TGG AGT GGT TCT CAG CAG GTT GAA CAA CCT ACT GGC TCT GTC CTC TGG ATG GCC CCA GAG GTG ATC CGA
Asp Phe Gly Leu Ala Thr Val Lys Ser Arg Trp Ser Gly Ser Gln Gln Val Glu Gln Pro Thr Gly Ser Val Leu Trp Met Ala Pro Glu Val Ile Arg
                                                                                                                                1782
ATG CAG GAT AAC CCA TTC AGT TTC CAG AGT TAC TCC GAT GTC TAC TCG TAT GCC ATC GTA TTG TAT GAA CTG ATG ACG GGG GAG CTT CCT TAT TCT CAC ATC
Met Gln Asp Asn Pro Phe Ser Phe Gln Ser Tyr Ser Asp Val Tyr Ser Tyr Ala Ile Val Leu Tyr Glu Leu Met Thr Gly Glu Leu Pro Tyr Ser His Ile
       Exon 16
       |                                                                                                                          1881
AAC AAC CGA GAT CAG ATC ATC TTC ATG GTG GGC CGA GGA TAT GCC TCC CCA GAT CTT AGT AAG CTA TAT AAG AAC TGC CCC AAA GCA ATG AAG AGG CTG
Asn Asn Arg Asp Gln Ile Ile Phe Met Val Gly Arg Gly Tyr Ala Ser Pro Asp Leu Ser Lys Leu Tyr Lys Asn Cys Pro Lys Ala Met Lys Arg Leu
                                                                                 Exon 17
                                                                                 |                                                1980
GTA GCT GAC TGT GTG AAG AAA GTA AAG GAA GAG AGG CCT CTT TTT CCC CAG ATC CTG TCT TCC ATT GAG CTG CTC CAA CAC TCT CTA CCG AAG ATC AAC
Val Ala Asp Cys Val Lys Lys Val Lys Glu Glu Arg Pro Leu Phe Pro Gln Ile Leu Ser Ser Ile Glu Leu Leu Gln His Ser Leu Pro Lys Ile Asn
                                                                                                                                  2079
CGG AGC GCT TCC GAG CCA TCC TTG CAT CGG CTG CAT CCG GCA GCC CAC ACT GAG GAT ATC AAT GCT TGC ACG CTG ACC ACG TCC CCG AGG CTG CCT GTC TTC TAG TTG
Arg Ser Ala Ser Glu Pro Ser Leu His Arg Leu His Pro Ala Ala His Thr Glu Asp Ile Asn Ala Cys Thr Leu Thr Thr Ser Pro Arg Leu Pro Val Phe
                                                                                                                                  2199
ACTTTGCACC TGTCTTCAGG CTGCCAGGGG AGGAGGAGAA GCCAGCAGGC ACCACTTTTC TGCTCCCTTT CTCCAGAGGC AGAACACATG TTTTCAGAGA AGCTCTGCTA AGGACTTCT
                                                                                                                                  2319
AGACTGCTCA CAGGGCCTTA ACTTCATGTT GCCTTCTTTT CTATCCCTTT GGGCCCTGGG AGAAGGAAGC CATTTGCAGT GCTGGTGTGT CCTGCTCCCT CCCCACATTC CCCATGCTCA
                                                                                                                                  2439
AGGCCCAGCC TTCTGTAGAT GCGCAAGTGG ATGTTGATGG TAGTACAAAA AGCAGGGGCC CAGCCCCAGC TGTTGGCTAC ATGAGTATTT AGAGGAAGTA AGGTAGCAGG CAGTCCAGCC
                                                                                                                                  2559
CTGATGTGGA GACACATGGG ATTTTGGAAA TCAGCTTCTG GAGGAATGCA TGTCACAGGC GGGACTTTCT TCAGAGAGTG GTGCAGCGCC AGACATTTTG CACATAAGCC ACCAAACAGC

FIG.9C
```

```
                                                                                          2679
CCAGGACTGC CGAGACTCTG GCCGCCCGAA GGAGCCTGCT TTGGTACTAT GGAACTTTTC TTAGGGGACA CGTCCTCCTT TCACAGCTTC TAAGGTGTCC AGTGCATTGG GATGGTTTTC
                                                                                          2799
CAGGCAAGGC ACTCGGCCAA TCCGGATCTC AGCCCTCTCA GGAGCAGTCT TCCATCATGC TGAATTTTGT CTTCCAGGAG CTGCCCCTAT GGGGCGGGCC GCAGGGCCAG CCTGTTTCTC
                                                                                          2919
TAACAAACAA ACAAACAAAC AGCCTTGTTT CTCTAGTCAC ATCATGTGTA TACAAGGAAG CCAGGAATAC AGGTTTTCTT GATGATTGG GTTTTAATTT TGTTTTATTT GCACCTGACA
                                 2986
AAATACAGTT ATCTGATGGT CCCTCAATTA TGTTATTTTA ATAAAATAAA TTAAATTTAA AAAAAA

AAATACAGTT ATCTGATGGT CCCTCAATTA TGTTATTTTA ATAAAATAAA TTAAATTTAG GTGTAATGGC CTCCTTTTAA AGTAATTCTG AGCTCACAAC TTGAATGCCC

CATTTGTTCA CCCTCTTCAG GATCAGAATT C
                      ‾‾‾‾‾‾‾‾
                       EcoRI
```

FIG.9D

```
TGACCCAATAAAGGGTGGAAGGCTGAGTCCCGCAGAGCCAATAACGAGAGTCCGAGAGGCGACGGAGGCGGACTCTGTGAGGAAACAGAGAAGAGAGGCCCAAGATGGAGACGCGGGCGGC       119

TGTAGCGGGGTGACAGGAGCCCCATGGCACCTGCCCAGCCCCACCTCAGCCCCATCTTGACAAAATCTAAGGCTCC ATG GAG CCA CCA CGG GGC CCC CCT GCC AAT GGG       227
                                                                             Met Glu Pro Pro Arg Gly Pro Pro Ala Asn Gly
                                                                              1                                       10

GCC GAG CCA TCC CGG GCA GTG GGC ACC GTC AAA GTA TAC CTG CCC AAC AAG CAA CGC ACG GTG GTG ACT GTC CGG GAT GGC ATG AGT GTC       317
Ala Glu Pro Ser Arg Ala Val Gly Thr Val Lys Val Tyr Leu Pro Asn Lys Gln Arg Thr Val Val Thr Val Arg Asp Gly Met Ser Val
                    20                                      30                                      40

TAC GAC TCT CTA GAC AAG CTG AAG GTG CGG GGT CTA AAT CAG GAC TGC TGT GTC GTC TAC CGA CTC ATC AAG GGA CGA AAG ACG GTC             407
Tyr Asp Ser Leu Asp Lys Leu Lys Val Arg Gly Leu Asn Gln Asp Cys Cys Val Val Tyr Arg Leu Ile Lys Gly Arg Lys Thr Val
                    50                                      60                                      70

ACT GCC ACA GCC ATT GCT CCC CTG GAT GGC GAG GAG CTC ATT GTC GAG GTC CTT GAA GAT GTC CCG CTG ACC ATG CAC AAT TTT                 497
Thr Ala Thr Ala Ile Ala Pro Leu Asp Gly Glu Glu Leu Ile Val Glu Val Leu Glu Asp Val Pro Leu Thr Met His Asn Phe
                    80                                      90                                     100
                                                          M+ / MA

GTA CGG AAG ACC TTC AGC TTC CGG CTG GCG TTC TGT GAC TTC TGC CTT AAG TTT CTG TTC CAT GGC TTC CGT TGC CAA ACC TGT GGC TAC AAG    587
Val Arg Lys Thr Phe Ser Phe Arg Leu Ala Phe Cys Asp Phe Cys Leu Lys Phe Leu Phe His Gly Phe Arg Cys Gln Thr Cys Gly Tyr Lys
                    110                                     120                                     130

TTC CAC CAG CAT TGT TCC TCC AAG GTC CCC ACA GTC TGT GTT GAC ATG AGT ACC AAC CGC CAA CAG TTC TAC CAC AGT GTC CAG GAT TTG        677
Phe His Gln His Cys Ser Ser Lys Val Pro Thr Val Cys Val Asp Met Ser Thr Asn Arg Gln Gln Phe Tyr His Ser Val Gln Asp Leu
                    140                                     150                                     160
```

FIG.10A

```
TCC GGA GGC TCC AGA CAG CAT GAG GCT CCC TCG AAC CGC CCC CTG AAT GAG TTG CTA ACC CCC CAG GGT CCC AGC CCC CGC ACC CAG CAC    767
Ser Gly Gly Ser Arg Gln His Glu Ala Pro Ser Asn Arg Pro Leu Asn Glu Leu Leu Thr Pro Gln Gly Pro Ser Pro Arg Thr Gln His
                170                             180                             190

TGT GAC CCG GAG CAC TTC CCC TTC CCT GCC CCA AAT GCC CCC CTA CAG CGC ATC CGC TCC ACG TCC ACT CCC AAC GTC CAT ATG GTC    857
Cys Asp Pro Glu His Phe Pro Phe Pro Ala Pro Asn Ala Pro Leu Gln Arg Ile Arg Ser Thr Ser Thr Pro Asn Val His Met Val
                200                             210                             220

AGC ACC ACG GCC CCC ATG GAC TCC AAC CTC ATC CAG CTC ACT GGC TTC AGC ACT GAT GCT GAT GCT GGT AGT AGA GGA GGT AGT GAT    947
Ser Thr Thr Ala Pro Met Asp Ser Asn Leu Ile Gln Leu Thr Gly Gln Ser Phe Ser Thr Asp Ala Ala Gly Ser Arg Gly Gly Ser Asp
                230                             240                             250

GGA ACC CCC CGG AGC CCA AGC CCA AGC GTG TCC TCG AGG AAG TCC CCA CAT TCC AAG TCA CCA GCA GAG CAG CGC GAG CGG    1037
Gly Thr Pro Arg Gly Ser Pro Ser Pro Ser Val Ser Ser Arg Lys Ser Pro His Ser Lys Ser Pro Ala Glu Gln Arg Glu Arg
                260                             270                             280

AAG TCC TTG GCC GAT GAC AAG AAA GTG AAG AAC CTG GGG TAC TGG GAT TCA GGC TAT TAC TGG GAG GTA CCA CCC AGT GAG GTG CAG    1127
Lys Ser Leu Ala Asp Asp Lys Lys Val Lys Lys Asn Leu Gly Tyr Trp Asp Ser Gly Tyr Tyr Trp Glu Val Pro Pro Ser Glu Val Gln
 *               *               290                             300                             310
         *

CTG CTG AAG AGG ATC GGG ACG GGC TCG TTT GGC ACC GTG TTT CGA GGG CGG TGG CAT GGC GAT GTG GCC GTG AAG GTG CTC AAG GTG TCC    1217
Leu Leu Lys Arg Ile Gly Thr Gly Ser Phe Gly Thr Val Phe Arg Gly Arg Trp His Gly Asp Val Ala Val Lys Val Leu Lys Val Ser
                320                             330                       †     340

CAG CCC ACA GCT GAG CAG CAG GCT CAG TTC AAG AAT GAG ATG CAG GTG CTC AGG AAG ATG CGA CAT GTC AAC ATC TTG CTG TTT ATG GGC    1307
Gln Pro Thr Ala Glu Gln Gln Ala Gln Phe Lys Asn Glu Met Gln Val Leu Arg Lys Met Arg His Val Asn Ile Leu Leu Phe Met Gly
                350                             360                             370

TTC ATG ACC CGG CCG GGA TTT GCC ATC ATC ACA CAG TGG TGT GAG GGC TCC AGC CTC TAC CAT CAC CTG CAT GTG GCC GAC ACA CGC TTC    1397
Phe Met Thr Arg Pro Gly Phe Ala Ile Ile Thr Gln Trp Cys Glu Gly Ser Ser Leu Tyr His His Leu His Val Ala Asp Thr Arg Phe
                380                             390                             400
```

FIG.10B

```
GAC ATG GTC CAG CTC ATC GAC GTG GCC CGG CAG ACT GCC CAG GGC ATG GAC TAC CTC CAT GCC AAG AAC ATC ATC CAC GAT CTC AAG   1487
Asp Met Val Gln Leu Ile Asp Val Ala Arg Gln Thr Ala Gln Gly Met Asp Tyr Leu His Ala Lys Asn Ile Ile His Arg Asp Leu Lys
                410                             420                             430
TCT AAC AAC ATC TTC CTA CAT GAG GGG CTC ACG GTG AAG ATC GGT GAC TTT GGC TTG GCC ACA GTG AAG ACT CGA TGG AGC GGG GCC CAG   1577
Ser Asn Asn Ile Phe Leu His Glu Gly Leu Thr Val Lys Ile Gly Asp Phe Gly Leu Ala Thr Val Lys Thr Arg Trp Ser Gly Ala Gln
                440                             450                             460
CCC TTG GAG CAG CCC TCA GGA TCT GTG GCA GCT GAG GTG ATC CGT ATG CAG GAC CCG AAC CCC TAC AGC TTC CAG TCA GAC   1667
Pro Leu Glu Gln Pro Ser Gly Ser Val Leu Trp Met Ala Ala Glu Val Ile Arg Met Gln Asp Pro Asn Pro Tyr Ser Phe Gln Ser Asp
                470                             480                             490
GTC TAT GCC TAC GGG GTT GTG CTC TAC GAG CTT ATG ACT GGC TCA CTG CCT TAC AGC CAC ATT GGC TGC CGT GAC CAG ATT ATC TTT ATG   1757
Val Tyr Ala Tyr Gly Val Val Leu Tyr Glu Leu Met Thr Gly Ser Leu Pro Tyr Ser His Ile Gly Cys Arg Asp Gln Ile Ile Phe Met
                500                             510                             520
GTG GGC CGT GGC TAT CTG TCC CCG GAC CTC AGC AGC AAA ATC TCC AAC TGC CCC AAG ATG CGG CGC CTG CTG TCT GAC TGC CTC AAG   1847
Val Gly Arg Gly Tyr Leu Ser Pro Asp Leu Ser Ser Asn Cys Pro Lys Met Arg Arg Leu Leu Ser Asp Cys Leu Lys
                530                             540                             550
TTC CAG CGG GAG CGG CCC CTC TTC CCC CAG ATC CTG GCC ACA ATT GAG CTG CTG CAA CGG TCA CTC CCC AAG ATT GAG GCC AGT GCC   1937
Phe Gln Arg Glu Arg Pro Leu Phe Pro Gln Ile Leu Ala Thr Ile Glu Leu Leu Gln Arg Ser Leu Pro Lys Ile Glu Ala Ser Ala
                560                             570                             580
TCG GAA CCC TCC TTG CAC CGC ACC CAG GCC GAT GAG TTG CCT GCC CTA CTC AGC GCA GCC CGC CTT GTG CCT TAG GCCCCGCCCAAGCCA   2030
Ser Glu Pro Ser Leu His Arg Thr Gln Ala Asp Glu Leu Pro Ala Cys Leu Leu Ser Ala Ala Arg Leu Val Pro
                590                             600                             606

CCAGGGAGCCAATCTCAGCCCTCCACGCCAAGGAGCCTTGCCCACCAGCACTCTCTGCCCTGATGCTGCCTCAGGATCCCCATTCCCACCCTGGGAGATGAGGGGG   2117
```

FIG. 10C

TCCCCATGTGCTTTCCAGTTCTTCTGGAATTGGGGACCCCCGCCAAAGACTGAGCCCCCTGTCTCCTCCATCATTGGTTCCTCTTGGCTTTGGGGATACTTCTAAATTTTGGGAG 2268

CTCCTCCATCTCCAATGGCTGGGATTGTGCTGGCAGGGATTCCACTCAGAACCTCTCTGGAATTTGTGCTGATGTGCCTTCCACTGGATTTGGGGTTCCCAGCACCCCATGTGGATTTT 2387

GGGGGGTCCCTTTTGTGTCTCCCCGCCATTCAAGGACTCCTCTCTCTTTCTTCACCAAGAAGCACAGAATTC

FIG.10D

```
                    10                    30                    50                    70                    90
GGGCAATATATCTGGAGGCCTATGAAGAATACACCAGCAAGCTAGATGCACTCCAACAAAGAGAACAACAGTTATTGGAATCTCTGGGAACGGAACTGA
                   110                   130                   150                   170                   190
TTTTTCTGTTCTGAGCTCTGCATCAATGGATACCGTTACATCTTCTCCTCTTCTTCAGCCTTTCAGTGCTACCTTCATCTCTTTCAGTTTTCAAAATCCC
                                          MetAspThrValThrSerSerSerLeuSerValLeuProSerLeuSerValPheGlnAsnPro
                   210                   230                   250                   270                   290
ACAGATGTGGCACGGGAGCACGGGAGCAACCCCAAGTCACCCACAAAAACCTATGCTTAGAGTCTTCCTGCCCAACAGAGGACAGTGGTACCTGCAAGGTGTGGAG
ThrAspValAlaArgSerAsnProLysSerProGlnLysProIleValArgValPheLeuProAsnLysGlnArgThrValValProAlaArgCysGlyV
                   310                   330                   350                   370                   390
TTACAGTCCGAGACAGTCTAAAGAAAGCACTGATGATGAGAGGTCTAATCCCAGAGTGCTGTGTTACAGAATTCAGGATGGAGAAGAAAACCAAT
alThrValArgAspSerLeuLysLysAlaLeuMetMetArgGlyLeuIleProGluCysCysAlaValTyrArgIleGlnAspGlyGluLysLysProIl
                   410                   430                   450                   470                   490
TGGGACACTGATATTTCCTGGCTTACTGGAGAAGAATTGCATGTGGAAGTGTTGGAAGAATGTCCACTTACAACACAACTTTGTACGAAAAACG
eGlyTrpAspThrAspIleSerTrpLeuThrGlyGluGluLeuHisValGluValLeuGluAsnValProLeuThrThrHisAsnPheValArgLysThr
                   510                   530                   550                   570                   590
TTTTCACCTTAGCATTTGTGACTTTTGTGAAAGCTGCTTTTCCGCTGTCAAACATGGTTATAAATTTCACCAGCGTTGTAGTACAG
PheThrLeuAlaPheCysAspPheCysArgLysLeuLeuPheGlyPheArgCysGlnThrCysGlyTyrLysPheHisGlnArgCysSerThrG
                   610                   630                   650                   670                   690
AAGTTCCACTGATGTGTTAATTATGACCAACTTGATTGCTGTTGTCTCCAAGTTCTTTGAACACCCAATACCACCAGGAAGAGGGTCCTTAGC
luValProLeuMetCysValAsnTyrAspGlnLeuLeuPheValSerLysPhePheGluHisProIleProGlnGluAlaSerLeuAl
                   710                   730                   750                   770                   790
AGAGACTGCCTAACATCTGGATCATCCCCTTCCGACCCGCCCTGGACTCTATTGGGCCCAAATTCTCACCAGTCCGTCTCCTTCAAAATCCATTCCA
aGluThrAlaLeuThrSerGlySerSerProSerAspArgSerAspSerIleGlyProGlnIleLeuThrSerProSerProSerLysSerIlePro
                   810                   830                   850                   870                   890
ATTCCACAGCCCTTCCGACCAGCAGATGAAGATCATCGAAATCAATTTGGGCAACGAGACCGATCCTCATCAGTCCCAATGTGCATATAAACACAATAG
IleProGlnProPheArgProAlaAspHisArgAspArgSerSerAlaProAsnValHisIleAsnThrIleG
                   910                   930                   950                   970                   990
```

FIG. 11A

```
AACCTGTCAATATTGATGACTTGATTAGAGACCAAGGATTTCGTGGTGATGGAGGATCAACCACCAGGTTTGTCTGCTACCCCCCCTGCCTCATTACCTGG
luProValAsnIleAspAspLeuIleArgArgAspGlnGlyPheArgGlyAspGlyPheThrThrGlyLeuSerAlaThrProProAlaSerLeuProGl
      1010              1030              1050              1070              1090
CTCACTAACGTGAAAGCCTTACAGGACCCTCAGCGAGAAAGGAAGTCATCTTCATCCTCAGAGACAGGAATCGAATGAAAACACTT
ySerLeuThrAsnValLysAlaLeuGlnArgGluArgLysSerProGlyProGlnArgLysSerSerSerSerGluAspArgAsnArgMetLysThrLeu
      1110              1130              1150              1170              1190
                                                                      *      *
GGTAGACGGGACTCGAGTGATGATTCCTGATGGGCAGATTACAGTGGGACAAAGAATTGGATCTGGATCATTGGAACAGTCTACAAGGGAA
GlyArgArgAspSerSerAspAspTrpGluIleProAspGlyGlnIleThrValGlyGlnArgIleGlySerPheGlyThrValTyrLysGlyL
      1210              1230              1250              1270              1290
AGTGGGCATGGTGATGTGGCAGTGAAAATGTTGAATGTGACAGCACCTACACCTCAGCAGTTACAAGCCTTCAAAAATGAAGTAGGAGTACTCAGGAAAAC
ysTrpHisGlyAspValAlaValLysMetLeuAsnValThrAlaProThrProGlnGlnLeuGlnAlaPheLysAsnGluValGlyValLeuArgLysTh
      1310              1330              1350              1370              1390
ACGACATGTGAATATCTCCTACTCTTCATGGGCTATTCCACAAAGCCACAACTGGCTATTGTTACCCAGTGGTGTGAGGCTCCAGCTTGTATCACCATCTC
rArgHisValAsnIleLeuLeuPheMetGlyTyrSerThrLysProGlnLeuAlaIleValThrGlnTrpCysGluGlySerLeuTyrHisHisLeu
      1410              1430              1450              1470              1490
CATATCATTGAGACCAAATTTGAGATCATCAAACTTATAGATATTGCACGACAGAGCATGGATTACTTACACGCCAAGTCAATCATCCACA
HisIleIleGluThrLysPheGluMetIleLysLeuIleAspIleAlaArgGlnThrAlaGlnGlyMetAspTyrLeuHisAlaLysSerIleIleHisA
      1510              1530              1550              1570              1590
GAGACCTCAAGAGTAATAATATATTCTTCATGAAGACCTCACAGTAAAAATAGGTGATTTTGGTCTAGCTACAGTGAAATCTGATGGAGTGGGTCCCA
rgAspLeuLysSerAsnAsnIlePheLeuHisGluAspLeuThrValLysIleGlyAspPheGlyLeuAlaThrValLysSerArgTrpSerGlySerHi
      1610              1630              1650              1670              1690
                       +    +    +                                              -   -   -
TCAGTTTGAACAGTTGTCTGGATCCATTTGTGGATGGCACCAGAAGTCATCAGAATGCAAGATAAAAATCCATACAGTTTCAGTCAGATGTATATGCA
sGlnPheGluGlnLeuSerGlySerIleLeuTrpMetAlaProGluValIleArgMetGlnLysAspLysAsnProTyrSerPheGlnSerAspValTyrAla
      1710              1730              1750              1770              1790
```

FIG. 11B

```
TTTGGAATTGTTCTGTATGAATTGATGACTGGACAGTTACCTTATTCAAACATCAACAACAGGGACCAGATAATTTTATGGTGGGACGAGGATACCTGT
PheGlyIleValLeuTyrGluTyrGlyLeuMetThrGlyGlnLeuProTyrSerAsnIleAsnArgAspGlnIleIlePheMetValGlyArgGlyTyrLeuS
      1810                   1830                  1850                    1870                1890
CTCCAGATCTCAGTAAGGTACGGAGTAACTGTCCAAAAGCCATGTCCAAAAGAGAGATTAATGGCAGAGTGCCTCAAAAGAAAAGAGATGAGAGACCACTCTTTCC
erProAspLeuSerLysValArgSerAsnCysProLysAlaMetLysArgLeuMetAlaGluCysLeuLysLysLysArgAspGluArgProLeuPhePr
      1910                   1930                  1950                   1970                  1990
CCAAATTCTCGCCTCTATTGAGCTGCTGGCCCGCTCATTGCCAAAATTCACCGCAGTGCATCAGAACCCTCCTTGAATCGGGCTGGTTTCCAAACAGAG
oGlnIleLeuAlaSerIleGluLeuLeuAlaArgSerLeuProLysIleHisArgSerAlaSerGluProSerLeuAsnArgAlaGlyPheGlnThrGlu
      2010                  2030                    2050                 2070                    2090
GATTTTAGTCTATATGCTTGTGCTTCTCCAAAAACACCCATCCAGGCAGGGGGATATGGTTGCTTTCCTGTCCACTGAAACAAATGAGTGAGAGAGTTCA
AspPheSerLeuTyrAlaCysAlaSerProLysThrProIleGlnAlaGlyTyrGlyAlaPheProValHis
    2110                     2130                    2150                2170                 2190
GGAGAGTAGCAACAAAAGGAAAAATAAATGAACATATGTTTGCTTATATGTTAAATTGAATAAATACTCTCTTTTTTTTTAAGGTGTGGAAAAAAAAAAAA
                    2210
AAAAAAAAAAAAAAAAAAAAAAAAAAAAAACCC
```

FIG.11C

RAF PROTEIN KINASE THERAPEUTICS

This application is a continuation of application Ser. No. 07/748,931, filed Aug. 23, 1991 now abandoned.

BACKGROUND OF THE INVENTION

Field of the Invention

The present invention relates, in general, to methods of inducing a therapeutic effect. In particular, the present invention relates to therapeutic uses of Raf protein kinases.

Background Information

Raf serine- and threonine-specific protein kinases are cytosolic enzymes that stimulate cell growth in a variety of cell systems (Rapp, U. R., et al. (1988) In The oncogene handbook; T. Curran, E. P. Reddy, and A. Skalka (ed.) Elsevier Science Publishers; The Netherlands, pp.213–253; Rapp, U. R., et al. (1988) Cold Spring Harbor Sym. Quant. Biol. 53:173–184; Rapp, U.R., et al. (1990) In: Curr. Top. Microbiol. Immunol. Potter and Melchers (eds), Berlin, Springer-Verlag 166:129–139). Three isozymes have been characterized: c-Raf (Raf-1) (Bonner, T. I., et al. (1986) *Nucleic Acids Res.* 14:1009–1015 see FIG. 9). A-Raf (Beck, T. W., et al. (1987) *Nucleic Acids Res.* 15:595–609 see FIG. 10), and B-Raf (Ikawa, S., et al. (1988) Mol. Cell. Biol. 8:2651–2654; Sithanandam, G. et al. (1990) Oncogene 5:1775 see FIG. 11). These enzymes differ in their expression in various tissues. Raf-1 is expressed in all organs and in all cell lines that have been examined, and A- and B-Raf are expressed in urogenital and brain tissues, respectively (Storm, S. M. (1990) Oncogene 5:345–351).

Raf genes are proto-oncogenes: they can initiate malignant transformation of cells when expressed in specifically altered forms. Genetic changes that lead to oncogenic activation generate a constitutively active protein kinase by removal or interference with an N-terminal negative regulatory domain of the protein (Heidecker, G., et al. (1990) Mol. Cell. Biol. 10:2503–2512; Rapp, U. R., et al. (1987) In Oncogenes and cancer S. A. Aaronson, J. Bishop, T. Sugimura, M. Terada, K. Toyoshima, and P. K. Vogt (ed.) Japan Scientific Press, Tokyo). Microinjection into NIH 3T3 cells of oncogenically activated but not wild-type versions of the Raf-protein prepared with *Escherichia coli* expression vectors results in morphological transformation and stimulates DNA synthesis (Rapp, U. R., et al. (1987) In Oncogenes and cancer; S. A. Aaronson, J. Bishop, T. Sugimura, M. Terada, K. Toyoshima, and P. K. Vogt (ed.). Japan Scientific Press, Tokyo; Smith, M. R., et al. (1990) Mol. Cell. Biol. 10:3828–3833). Thus, activated Raf-1 is an intracellular activator of cell growth. Raf-1 protein serine kinase is a candidate downstream effector of mitogen signal transduction, since Raf oncogenes overcome growth arrest resulting from a block of cellular ras activity due either to a cellular mutation (ras revertant cells) or microinjection of anti-ras antibodies (Rapp, U. R., et al. (1988) In The Oncogene Handbook, T. Curran, E. P. Reddy, and A. Skalka (ed.), Elsevier Science Publishers; The Netherlands, pp.213–253; Smith, M. R., et al. (1986) Nature (London) 320:540–543).

c-Ras function is required for transformation by a variety of membrane-bound oncogenes and for growth stimulation by mitogens contained in serum (Smith, M. R., et al. (1986) Nature (London) 320:540–543). Raf-1 protein merine kinase activity is regulated by mitogens via phosphorylation (Morrison, D. K., et al. (1989) Cell 58:648–657), which also effects subcellular distribution (Olah, Z., et al. (1991) Exp. Brain Res.84:403; Rapp, U. R., et al. (1988) Cold Spring Harbor Sym. Quant. Biol. 53:173–184).

Raf-1 activating growth factors include platelet-derived growth factor (PDGF) (Morrison, D. K., et al. (1988) Proc. Natl. Acad. Sci. USA 85:8855–8859) colony-stimulating factor 1 (Baccarini, M., et al. (1990) EMBO J. 9:3649–3657), insulin (Blackshear, P. J., et al. (1990) J. Biol. Chem. 265:12131–12134; Kovacina, K. S., et al. (1990) J. Biol. Chem. 265:12115–12118), epidermal growth factor (EGF) (Morrison, D. K., et al. (1988) Proc. Natl. Acad. Sci. USA 85:8855–8859), interleukin 2 (Turner, B. C. et al. (1991) Proc. Natl. Acad. Sci. USA 88:1227), and interleukin 3 and granulocyte-macrophage colony-stimulating factor (Carroll, M. P., et al (1990) J. Biol. Chem. 265:19812–19817). Upon mitogen treatment of cells, the transiently activated Raf-1 protein serine kinase translocates to the perinuclear area and the nucleus (Olah, Z., et al. (1991) Exp. Brain Res. 84:403; Rapp, U. R., et al. (1988) Cold Spring Harbor Sym. Quant. Biol. 53:173–184). Cells containing activated Raf are altered in their pattern of gene expression (Heidecker, G., et al. (1989) In Genes and signal transduction in multistage carcinogenesis, N. Colburn (ed.), Marcel Dekker, Inc., New York. pp. 339–374), and Raf oncogenes activate transcription from Ap-1/PEA3-dependent promoters in transient transfection assays (Jamal, S., et al. (1990) Science 344:463–466; Kaibuchi, K., et al. (1989) J. Biol. Chem. 264:20855–20858; Wasylyk, C., at al. (1989) Mol. Cell. Biol. 9:2247–2250).

There are at least two independent pathways for Raf-1 activation by extracellular mitogens: one involving protein kinase C (PKC) and a second initiated by protein tyrosine kinases (Blackshear, P. J., et al. (1990) J. Biol. Chem. 265:12131–12134; Kovacina, K. S., et al. (1990) J. Biol. Chem. 265:12115–12118; Morrison, D. K., et al. (1988) Proc. Natl. Acad. Sci. USA 85:8855–8859; Siegel, J. N., et al.(1990) J. Biol. Chem. 265:18472–18480; Turner, B. C. et al. (1991) Proc. Natl. Acad. Sci. USA 88:1227). In either case, activation involves Raf-1 protein phosphorylation. Raf-1 phosphorylation may be a consequence of a kinase cascade amplified by autophosphorylation or may be caused entirely by autophosphorylation initiated by binding of a putative activating ligand to the Raf-1 regulatory domain, analogous to PKC activation by diacylglycerol (Nishizuka, Y. (1986) Science 233:305–312).

SUMMARY OF THE INVENTION

It is a general object of this invention to provide a construct comprising a DNA segment comprising a Raf gene in an antisense orientation downstream of a promoter.

It is a specific object of this invention to provide a method of inhibiting Raf expression comprising expressing an antisense Raf gene in a cell such that said Raf expression is inhibited.

It is a further object of the invention to provide a method of inhibiting Raf kinase activity comprising replacing a serine or threonine amino acid within the Raf gene for an amino acid not susceptible to phosphorylation.

Further objects and advantages of the present invention will be clear from the description that follows.

BRIEF DESCRIPTION OF TEE DRAWINGS

FIG. 1. Schematic diagram of murine and human c-raf-1 cDNAs and expression plasmids used. GMA and GMS contain Stu1 restriction fragments of the mouse c-raf-1 cDNA. HCR an N-terminal HincII fragment of the human cDNA. p301 consists of all the coding sequence of a mutant human c-raf-1 cDNA. The lysine(375) to tryptophan (K→W) mutation in the ATP-binding site is indicated (Heidecker, G. et al. *Molec. Cell. Biol*, 10:2503–2512 (1990)). Restriction fragments were cloned in both sense and antisense orientation. NIH/3T3 cells were transfected with sense and antisense plasmids, and with the pMNC vector as control. G418-resistant (400 μg ml$^{-1}$) colonies containing more than 50 cells were counted after three weeks. The pMNC vector served as internal standard. The experiment was repeated three times (twice for HCR) with different batches of plasmid preparations. Variations between experiments were in the order of 10% but did not affect the ratios between the different constructs shown. CR1-3, conserved regions; ATP, ATP-binding domain; LTR, mouse Moloney virus long terminal repeat; NEO, neomycin-resistance gene; CMV, cytomegalovirus immediate early promoter.

FIG. 2. Morphological reversion of raf-transformed cells by transfection with raf antisense and mutant constructs. a. p48 raf-transformed 208/F12 (Schultz, A. M. et al. *Oncogene* 2:187–193 (1988)) or b. v-raf-transformed F4 (Rapp, U. R., et al. *Proc. Natl. Acad. Sci. U.S.A.* 80:4218–4222 (1983)) fibroblasts were transfected with plasmids p301-1 (sense) and 301-2 (antisense) or GMS-7 (sense) and GMS-8 (antisense), respectively, as well as with the pMNC vector. Monolayer growth with minor irregularities and a decreased ability to form soft agar colonies was categorized as partial reversion. Flat clones showed no areas of overgrowth and did not form colonies in soft agar. c. A representative analysis of Raf protein expression in individual cell clones. t. Transformed; im. intermediate; f. flat (clone GMS-8/2); f* (clone GMS-8/3).

FIG. 3. Mitogen responsiveness and proliferative capacity of Raf-depleted cells. a. DNA synthesis induced by serum or TPA in serum-starved cells is depicted as the number of nuclei incorporating $^3$ H-thymidine. b. Long term growth curves GMS-7 is a pool of 10 clones transfected with sense DNA. GMS-8/2 and GMS-8/3 are flat clones reverted with antisense DNA. a, ▩ starved cells; □, TPA-induced cells; ■, SERUM-induced cells. b,□, F4; ■, GMS-7b; O GMS-8/2; O GM-8/3.

Figure 4:
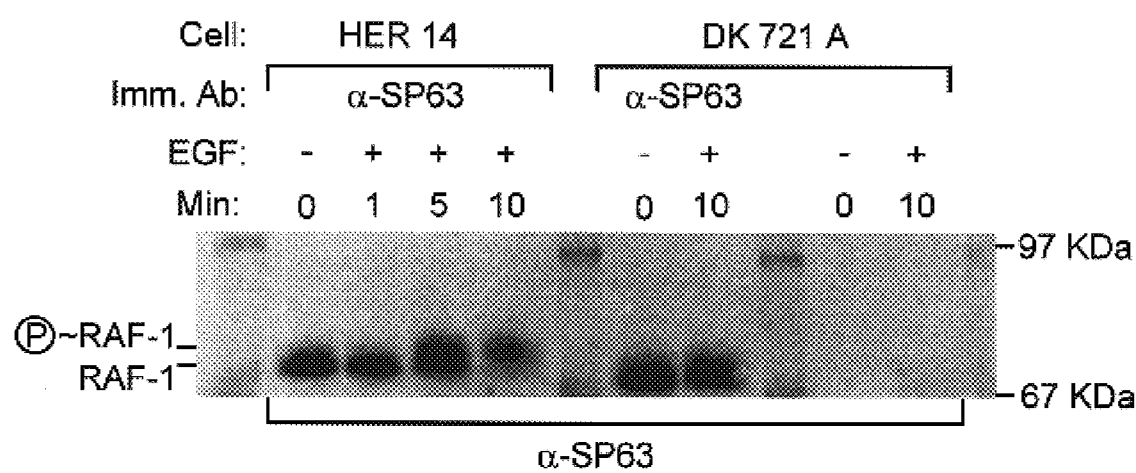

FIG. 4. Time course of Raf-1 mobility shift upon growth factor treatment. Cells (10$^7$) expressing either wild-type (HER14) or kinase-negative (DK721A) EGF-R were stimulated at 37° C. with 40 nM EGF for the times indicated, lysed, and subjected to immunoprecipitation with anti-SP63 polyclonal antiserum. Immunoprecipitated proteins were separated by 7.5% SDS-PAGE, transferred to nitrocellulose, and probed with the same antiserum. Immunoreactive proteins were detected with $^{125}$I-labeled protein A, and autoradiographs were exposed for 12 h. Each lane represents immunoprecipitates from 10$^7$ cells. Lanes: 2 through 5. HER14 cell; 7 and 8, DK721A cells 9 and 10, DK721A cells with competing SP63 peptide (10 μg/ml); 1, 6, 9, and 11, marker proteins of 97 and 67 kDa.

Figure 5:
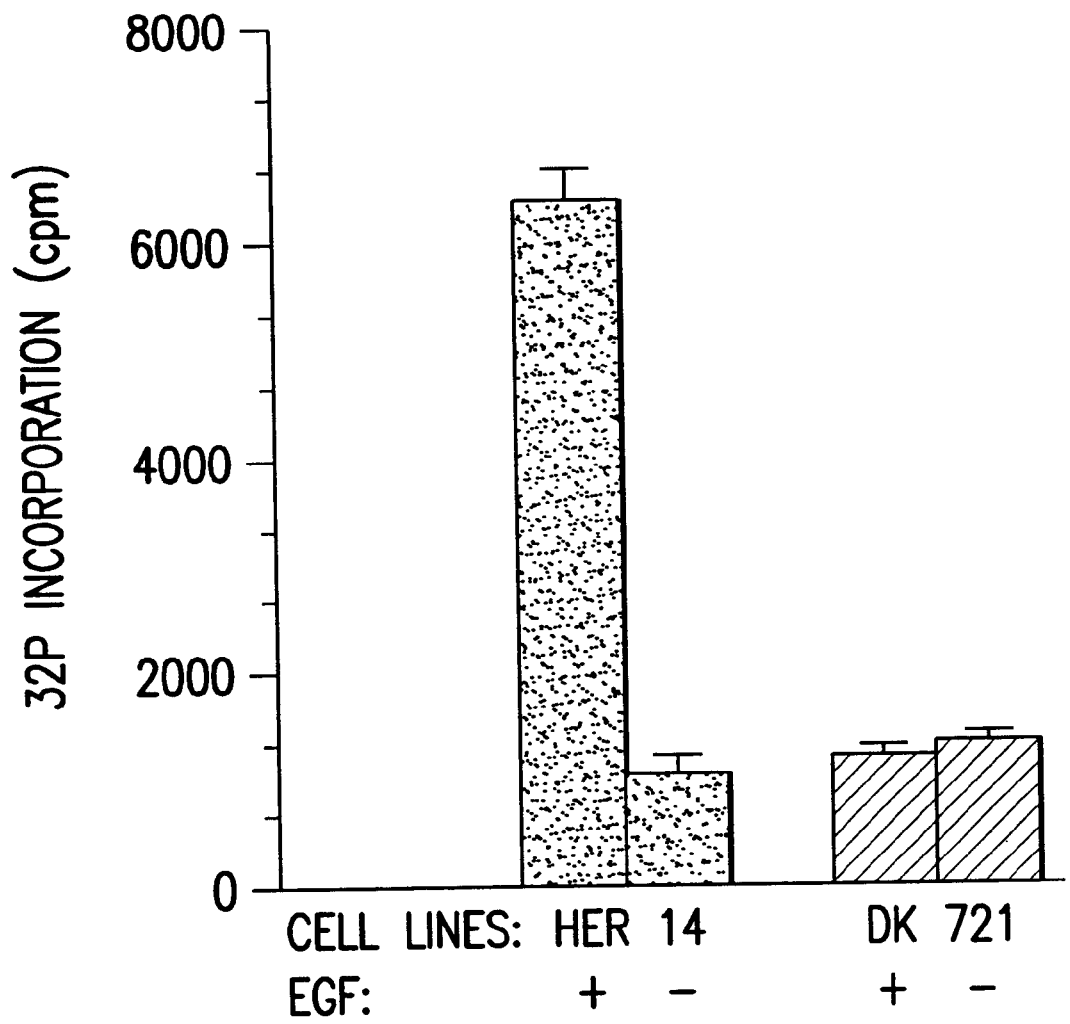

FIG. 5. Kinase activity upon EGF treatment HER14 and DK721A cells. Monolayer cultures of HER14 or K721A cells were incubated in the presence or absence of 40 nM EGF for 10 min at 37° C. Lysates were centrifuged, and the resulting supernatants were immunoprecipitated with Raf-1 antiserum. Immunocomplexes were assayed for kinase activity using peptide (IVQQFGFQRRASDDGKLTD) (SEQ ID NO:1) as (SEQ ID NO: 1) substrate. In the absence of peptide, immune complex kinase assays with unstimulated cells yielded ≤5% of counts observed in the peptide assay with stimulated cells. No counts were incorporated when a modified version of this peptide was used, in which serine in position 12 was replaced by alanine, and position 5 retained the Raf-1-specific tyrosine.

Figure 6A:
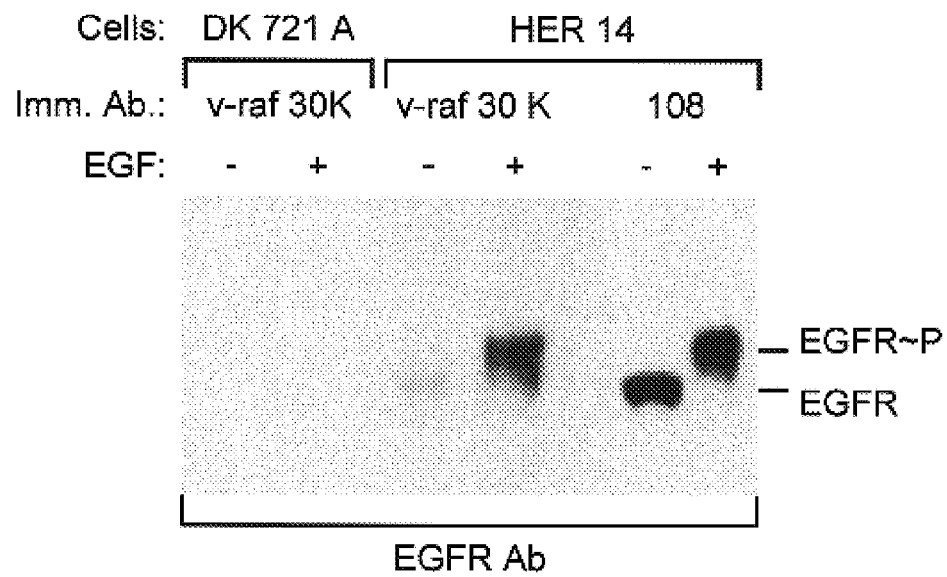
Figure 6B:
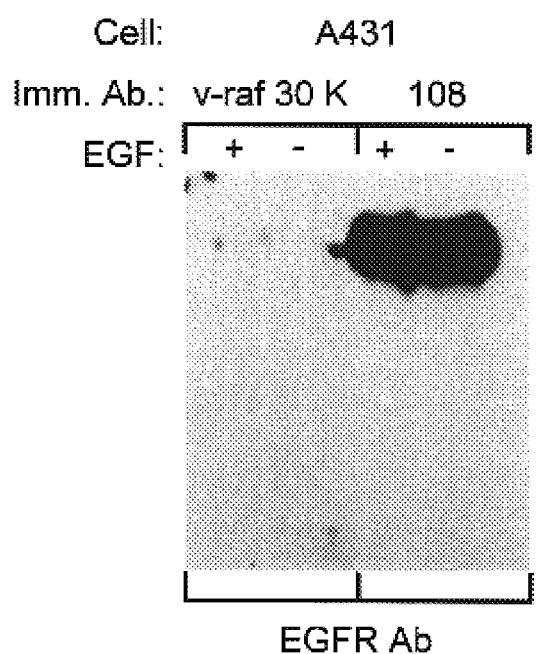
Figure 6C:
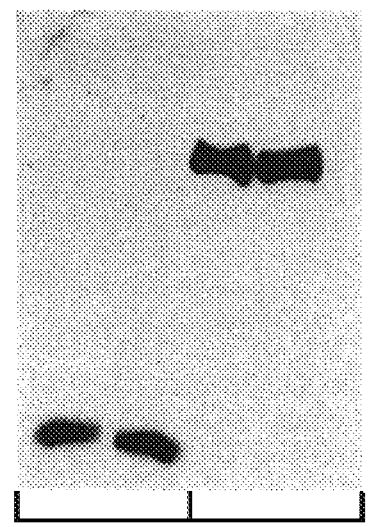

FIG. 6. Association of Raf-1 with ligand-activated EGF-R in HER14, DK721A, or A431 cells. Density-arrested and serum-starved HER14, DK721A, or A431 cells were stimulated for 10 min with 40 nM EGF at 37° C. before lysis with RIPA buffer and immunoprecipitation. (A) Immunoprecipitates from HER14 and DK721A cells with anti-v-Raf 30K polycolonal antiserum or with a monoclonal EGF-R antibody (108) were subjected to 7.5% SDS-PAGE and transferred to nitrocellulose. EGF-R was detected by incubating with a polyclonal antiserum (RK2) against the EGF receptor (Margolis, B., et al. (1989) Cell 57:1101–1107), followed by $^{125}$I-labeled protein A labeling. Exposure times for immunoblots were 3 days (lanes 1 through 4) or 1 day (lanes 5 and 6). (B and C) Immunoprecipitates from EGF-treated and control A431 cells with Raf-1 specific anti-v-Raf 30K antiserum or monoclonal anti-EGF-R antibody 108 were blotted, and the blots were developed sequentially with EGF-R antiserum RK2 (B) and anti-v-Raf 30K (C). Exposure times were 3 days and 1 day for panels B and C, respectively.

Figure 7:
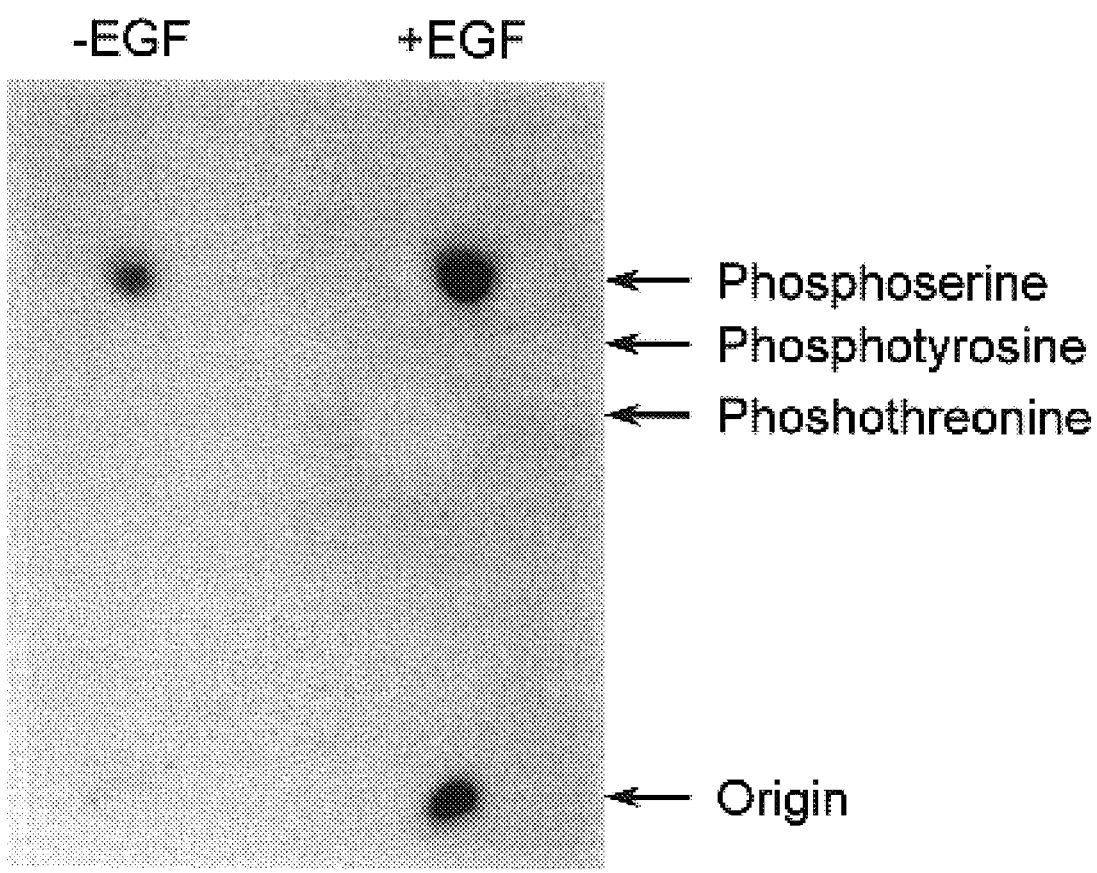

FIG. 7. Phosphoamino acid analysis of the immunoprecipitated Raf-1 protein from EGF-treated and untreated HER14 cells, HER14 cells (10$^7$) were phosphate starved for 16 h, labeled with 1 mCi of [$^{32}$P]phosphate for 3 h at 37° C., and treated with 40 nM EGF for 10 min at 37° C. Cells were lysed in RIPA buffer and immunoprecipitated. Proteins were separated by 7.5% SDS-PAGE, the Raf-1 bands were cut out of the gel, and the protein was electroeluted. From the electroeluted Raf-1 protein 1,960 cpm was recovered from the EGF-treated cells and 1,111 cpm was recovered from the untreated cells. The proteins were hydrolyzed for 2 h at 110° C. in 6 N hydrocloric acid. Phosphoamino acid analysis was performed at pH 1.8. as described by Cooer et al. (Cooper, A. A., et al. (1983) Methods in Enzymol. 99:387–402). The Raf-1 protein showed a shift in mobility when part of the electroeluted protein was rerun on 7.5% SDS-PAGE.

Figure 8:
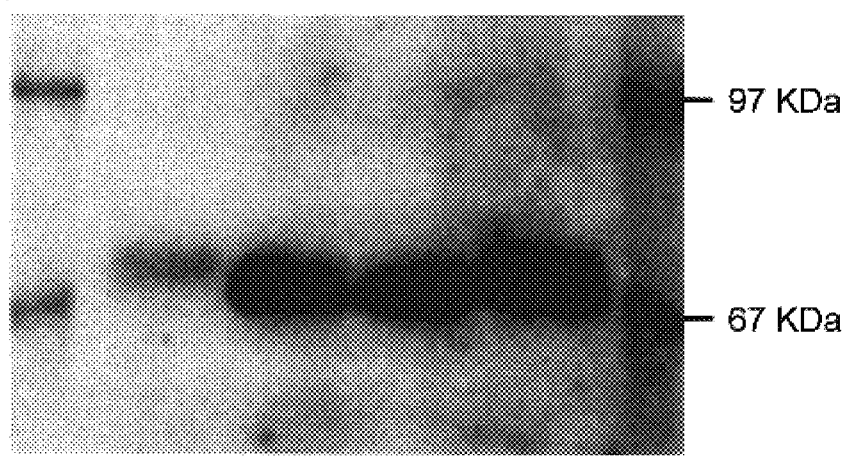

FIG. 8. Independence of EGF mediated Raf-1 activation from PKC. HER14 cells (10$^7$) were incubated for 48 h with or without 200 ng TPA and stimulated with either 100 ng of TPA for 20 min at 37° C. Cells were lysed in RIPA buffer, equal amounts of protein were immunoprecipitated with anti-v-Raf 30-kDa antiserum and electrophoresed, and the separated proteins were blotted onto nitrocellulose. The blot was incubated with the same antibody and then labeled with $^{125}$I-labeled protein A.

FIGS. 9A, 9B, 9C, and 9D: The nucleotide sequence of raf cDNA (see SEQ ID NO:2) and the deduced amino acid sequence of the raf protein (see SEQ ID NO:3). The bottom two lines show the sequence of the 3' end of the human c-raf-1gene (see SEQ ID NO:8) aligned with the 3' end of the cDNA. The first nucleotide of each exon is indicated by an asterisk above the sequence.

FIGS. 10A, 10B, 10C, and 10D: Human A-raf cDNA (SEQ ID NO:4) and derived amino acid sequence (SEQ ID NO:5). Nucleotides are numbered to the right of each line and amino acids below the corresponding residue.

FIGS. 11A, 11B, and 11C: The nucleotide sequence of human B-raf cDNA (SEQ ID NO:6) and the deduced amino acid sequence of the B-raf protein (SEQ ID NO:7).

DETAILED DESCRIPTION OP THE INVENTION

The present invention relates to the Raf protein kinase inhibitors and methods of use thereof.

In one embodiment, the present invention relates to antisense expression constructs comprising a Raf protein kinase gene. Raf-1 function is inhibited by expressing c-raf-1 antisense RNA or kinase-defective c-raf-1 mutants. Antisense RNA for c-raf-1 interferes with proliferation of normal NIH/3T3 cells and reverts raf-transformed cells. In revertant cells, DNA replication induced by serum or TPA is eliminated or reduced proportionately to the reduction in Raf protein levels. Expression of a kinase-defective Raf-1 mutant (craf301) or a regulatory domain fragment (HCR) inhibits serum-induced NIH/3T3-cell proliferation and raf transformation even more efficiently. Inhibition by antisense RNA or craf301 blocks proliferation and transformation by Ki- and Ha-ras oncogenes. Thus, raf functions as an essential signal transducer downstream of serum growth factor receptors, protein kinase C and ras.

In another embodiment, the present invention relates to a method of inhibiting Raf expression comprising expressing an antisense Raf gene (more specifically, Raf-1) in a cell such that said Raf expression is inhibited.

In another embodiment, the present invention relates to inhibitory peptides of Raf derived from Raf kinase specific substrate sequences. Phosphorylation sites of Raf substrates can be determined which are expected to yield consensus phosphorylation site motifs for the various Raf isozymes. Studies which gave rise to the present invention demonstrate that Raf is the subject of autophosphorylation. In one preferred embodiment, consensus substrate peptides are altered by introduction of alanine for phosphorylation targets serine or threonine.

In another preferred embodiment, the present invention relates to a method of inhibiting Raf kinase activity comprising replacing a codon within the Raf gene encoding a serine or thrednine amino acid for a codon encoding an amino acid not suceptable to phosphorylation and transforming said gene into a cell such that said Raf activity is inhibited.

In yet another embodiment, the present invention relates to a method of inhibiting Raf kinase activity comprising modifying Raf by replacing a serine or threonine amino acid within Raf for an amino acid not suceptable to phosphorylation and delivering said modified Raf to a cell such that said Raf expression is inhibited.

The present invention is described in further detail in the following non-limiting examples (see Kolch W. et al (1991) Nature 349:426 and App et al. (1991) Molec. Cell. Biol. 11(2):913–919).

EXAMPLES

The following protocols and experimental details are referenced in the Examples that follow:

Expression Plasmid Construction pMNC digested with XhoI and BamHI was blunt ended with T4 DNA polymerase. The mouse and human cDNAs were cut with StuI or HincII, respectively, and appropriate sized fragments were ligated with the pMNC vector. GMA contains residues 1254–1426. and GMS 1427–1697 of the mouse cDNA, HCR 1-903 of the human c-raf-1 cDNA (Bonner et al. Nucleic Acids Res. 14:1009–1015 (1986)). The translation termination codon for HCR sense is provided by vector sequences resulting in the addition of nine amino acids. To construct p301-1 (sense orientation), an EcoRI-XbaI fragment of p628 (Bonner et al. Nucleic Acids Res. 14:1009–1015 (1986)) encompassing the coding sequence of a human c-raf-1 cDNA was cloned into BluescriptKS (Stratagene). Lysine(375) was changed to tryptophan by site-directed mutagenesis resulting in the creation of a unique BamHI site. This cDNA was transferred into the SacI-XhoI sites of pSVL (Pharmacia), then cloned into the XhoI-BamHI sites of pMNC as an XhoI-BamHI (partial digest) fragment. The corresponding antisense plasmid, p301-2, was generated by cloning the blunt-ended c-raf 301 EcoRi-XbaI fragment into blunt-ended pMNC.

Western Analysis with PBB1.

Cells were lysed in TBST (160 mM NaCr, 20 mM-Tris HCl, pH7.5, 2 mM EDTA, 1% Triton X-100, 1 mM PMSF). Lysates were adjusted to equal protein concentrations (Biorad protein assay kit). Raf proteins were precipitated with the monoclonal antibody PBB1 and analyzed by western blotting with the polyclonal serum #137 as described previously (Kolch, W. et al. Oncogene 6:713–720 (1990)).

Mitogen Responsiveness and Proliferative Capacity Assay $10^4$ cells were plated on cover slips and serum-starved for 24 h before incubation with 20% fetal calf serum (Gibco) or 100 ng ml$^{-1}$ TPA (Sigma). 14 h after addition of mitogens, cells were labelled with 1 $\mu$Ciml$^{-1}$ $^3$H-thymidine for 5 h. Cells were counter-stained with Giemsa and labelled nuclei were counted. For long-term growth curves. $10^5$ cells were seeded in six-well plates in DMEM medium supplemented with 10% FCS. Each day, one well was trypsinized and counted with a Coulter cell counter. All determinations were performed in triplicate.

Cell Maintenances

NIH 3T3 clone 2.2 cells devoid of endogenous EGF-R were transfected with wild-type (HER14) or kinase-negative (DK721A) receptors as described previously (Honegger, A. M., et al. (1987) Cell 51:199–209; Honegger, A. M. (1987) Mol. Cell. Biol. 7:4567–4571; Margolis, B., et al. (1989) Cell 57:1101–1107). In the case of the kinase-negative receptor mutant, the putative ATP binding lysine was substituted by an alanine (Honegger, A. M., et al. (1987) Cell 51:199–209; Honegger, A. M. (1987) Mol. Cell. Biol. 7:4567–4571). Cells were maintained in Dulbecco modified Eagle medium (DMEM) containing 10% (vol/vol) calf serum.

Preparations of Cytosolic Cell Extracts and Immunoprecipitations

Cells were grown in 75-cm$^2$ flasks in DHEM containing 10% calf serum until confluency and starved overnight in 0.05% calf serum. Before lysis, cells were exposed to 40 nM EGF for 0 min at 37° C. and rinsed three times in phosphate-buffered saline. Control cells were not exposed to EGF. Cells were lysed in TBST buffer (50 mM Trio hydrochloride (pH 7.3), 150 mM NaCl, 0.5% Triton X-100) or in RIPA buffer (50 mM Tris hydrochloride (pH 7.3), 150 mM NaCl, 1% Triton X-100, 0.5% desoxycholate, 0.1% sodium dodecyl sulfate (SDS), 5 mM EDTA, 1 mM dithiothreitol, 0.2 mM sodium orthovanadate, 25 mM sodium fluoride, 10 mM sodium pyrophosphate, 25 mM glycerophosphate). Insoluble material was removed by centrifugation at 4° C. for 30 min at 12,000×g. Protein concentrations were determined by the method of Bradford (Bradford, M. M. (1976) Anal. Bichem. 72:248–254). Immunoprecipitations were performed by incubating lysates with polyclonal rabbit antiserum against the v-Raf 30-kDa protein (Kolch, W., et al. (1988) Biochim. Biophys. Acta 949:233–239) or a polyclonal rabbit antiserum against a synthetic peptide (SP63) corresponding to the last 12 carboxy-terminal amino acids of the Raf-1 protein and protein A for 3 h at 4° C.

Western Immunoblotting

The immunoprecipitates were resolved by SDS-polyacrylamide gel electrophoresis (PAGE). The gels were electroblotted on nitrocellulose, and the blots were blocked with 5% (wt/vol) gelatin in TBST buffer and incubated with polyclonal antiserum against Raf-1 or EGF-R. After extensive washing with TBST buffer, the blot was labeled with $^{125}I$ staph protein A (Dupont NEN). Nonbound $^{125}I$ staph was removed by washing the blots with TBST buffer, and the dried membrane was exposed to x-ray film.

Immunocomplex Kinase Assay

Immunoprecipitates were washed three times with cold RIPA buffer and twice with kinase buffer (50 mM Tris hydrochloride (pH 7.3), 150 mM NaCl, 12.5 EM $MnCl_2$, 1 mM dithiothreitol, and 0.2% Tween 20). Immunocomplex kinase assays were performed by incubating immunoprecipitates from $10^6$ cells in 80 μl of kinase buffer with 20 μCi of [γ-$^{32}$P]ATP (10 mCi/ml) and 20 μl of the Raf-1 substrate peptide (5 mg/ml) for 30 min at 25° C. The sequence of the Raf-1 substrate peptide is IVQQFGFQRRASDDGKLTD (SEQ ID NO: 1). A control peptide had tyrosine in position 5, as does wild-type Raf-1, and alanine in place of serine in position 12. The assay was linear for at least 40 min. The phosphorylation reaction was terminated by spotting 15-μl aliquots of the assay mixture on a 2- by 2-cm Whatman P81 phosphocellulose filter. The filters were washed four times for 30 min in 1% orthophosphoric acid and air dried, and the amount of $^{32}P$ incorporated was determined by the Cerenkov method. No differences were observed when counts were compared between filters on which the whole reaction mix or only the supernatant was spotted. Peptide phosphorylation in this assay was verified by running the reaction products on 20% SDS gels.

Phosphoamino Acid Analysis

One-dimensional phosphoamino acid analysis was carried out as described by Cooper et al. (Cooper, A. A., et al. (1983) Methods in Enzymol. 99:387–402). Phosphoamino acids were separated at pH 1.8 (6% formic acid and 15% acetic acid) for 4 h at 7.50V.

Example 1

Antisense Experiments

Figure 2C:
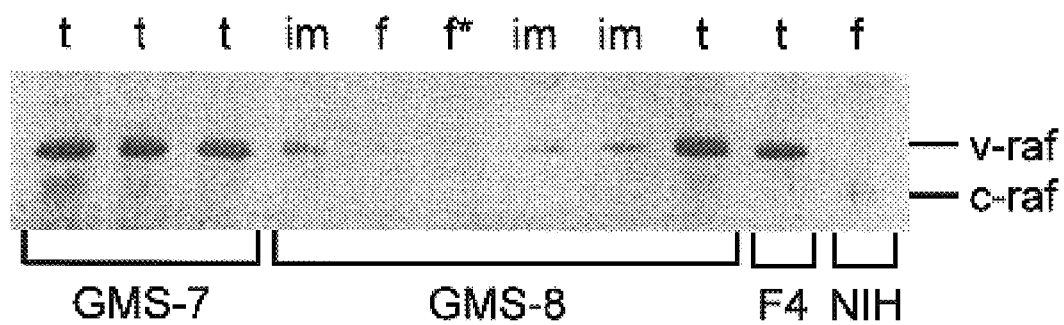

Portions of c-raf-1 cDNAs were expressed in sense and antisense orientation using the pMNC vector (FIG. 1). After transfection into NIH/3T3 cells the number of neomycin-resistant colonies was scored. Antisense constructs yielded roughly half the number of colonies as did the corresponding sense construct or the vector control, indicating that raf antisense RNA interferes with viability and/or proliferation. As NIH/3T3 cells express no B-raf and 10-fold less A-raf than Raf-1 (Storm, S. M. et al. Oncogene 5:345–351 (1990)), the effect can be ascribed to interference with Raf-1. Antisense colonies were generally smaller and grew slower than sense or vector control colonies. Ten out of ten antisense colonies showed barely detectable levels of Raf-1 protein, whereas levels in sense control clones were unchanged. An alternative approach to Raf-1 inhibition. used inactive mutants (Rapp, U. R. et al. The Oncogene Handbook (eds. E. P. Reddy, A. M. Skalka and T. Curran) 213–253 (Elsevier Science. The Netherlands, 1988); Heidecker, G. et al. Molec. Cell. Biol. 10:2503–2512 (1990)). A truncated Raf-1 protein (HCR) corresponding to conserved region 1 reduced colony numbers fourfold. A kinase-defective Raf-1 mutant protein, craf301 (plasmid p301-1), was even more efficient, decreasing colony yield about sevenfold (Heidecker, G. et al. Molec. Cell. Biol. 10:2503–2512 (1990)). The surviving colonies from these experiments could not be maintained as stable cell lines. raf-transformed cell-lines were examined for morphological reversion and inhibition of proliferation. p301 constructs were transfected into 208-F12 fibroblasts which overexpress a transforming mouse Raf-1 protein (Schultz, A. M. et al. Oncogene 2:187–193 (1988)). p301-2 caused partial or complete reversion of the transformed phenotype in approximately half the transfectants. Reversion correlated with loss of anchorage-independent growth. Again, p301-1 was more efficient than p301-2 (FIG. 2a). These clones were unstable, but cell-lines sufficiently stable for biochemical analysis were obtained after pGMS transfection of v-raf transformed cells, F4 (Rapp, U. R., et al. Proc. Natl. Acad. Sci. U.S.A. 80:4218–4222 (1983)). Neither pMNC nor the control plasmid GMS-7 was effective, whereas the antisense construct, GMS-8, completely or partially reverted F4 (FIG. 2b). Reduction of raf mRNA and protein levels correlated with the extent of reversion (FIG. 2c). In one clone, GMS-8/3 (marked f* in FIG. 2c), raf protein expression was undetectable. These cells grew extremely slowly, arresting at 50–60% confluency, and eventually died.

Figure 3B:
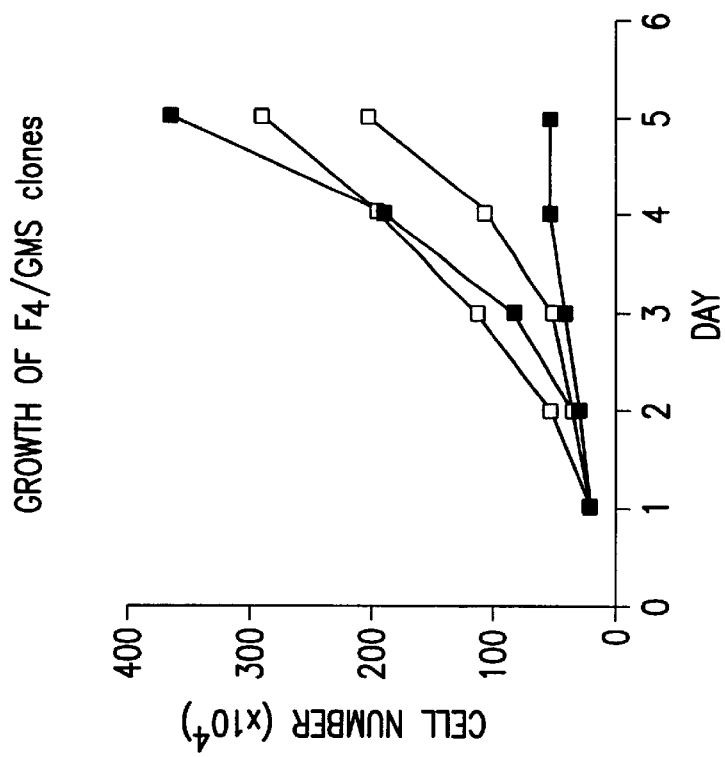
Figure 3A:
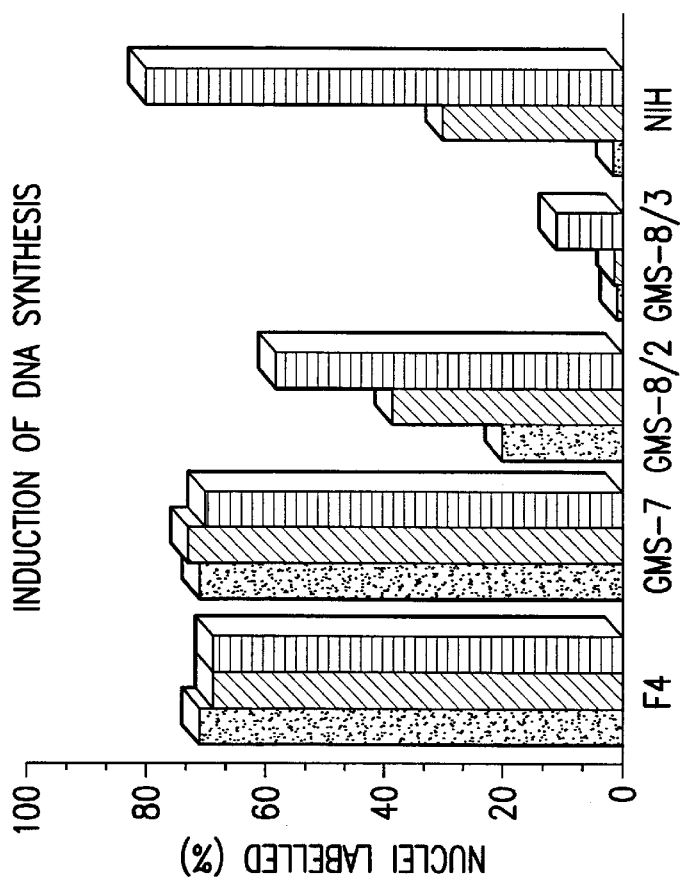

To measure the effects of raf-protein depletion on the mitogen response, the ability of serum and TPA to induce DNA synthesis in serum-starved cells was determined (FIG. 3a). F4 and GMS-7 cells synthesize DNA independently of mitogens. Constitutive DNA synthesis was diminished in GMS-8/2, which retained an inducible response similar to NIH/3T3 cells. GMS-8/3 was completely blocked in constitutive and TPA-inducible DNA replication. Serum-stimulation of GMS-8/3 was reduced seven-fold, and long-term growth was also severely diminished (FIG. 3b).

v-Ki-ras-transformed NIH/3T3 cells were transfected with the p301 plasmids (Table 1a). p301-1 and p301-2 reduced neomycin (neo)-resistant colony yield to a similar degree as in NIH/3T3 cells (FIG. 1), suggesting that Raf-1 is required for proliferation of ras-transformed cells. Morphological reversion of established ras-transformed cells was less efficient than of raf-transformed cells (FIG. 2). To test the effect of raf-inhibition on the initiation of ras-transformation, a constant amount of v-Ha-ras (pSV2neo/ras, Clanton, D. J. et al. Molec. Cell. Biol. 7:3092–3097 (1987)) plasmid was co-transfected with an equal or four-molar amount of the p301 vectors (Table 1b). Although the neomycin resistance of pMNC-based plasmids accounted for a background of flat neo colonies that presumably did not express pSV2neo/ras, transfection with p301 vectors markedly increased the number of morphological revertants at the expense of transformed colonies. The inhibition was dose-dependent and almost complete at four-molar excess of p301-1.

Thus, NIH/3T3 cells RAf-1 kinase functions downstream of membrane receptors and ras proteins and is essential for growth-induction by serum factors and protein kinase C. Membrane receptor systems can now be examined individually for Raf-1-dependence by inhibition with the blocking constructs described herein. Furthermore, the proposed position of raf in the communication pathway between cell membrane and nucleus makes raf an attractive target for the design of novel antiproliferative agents, especially as this data show that raf inhibition is dominant over transformation by ras and by implication by other non-nuclear oncogenes.

TABLE I raf-inhibition blocks ras-mediated proliferation and transformation a) v-Ki-ras cell transfection
   Yield of neo' Morphology of neo' colonies

| Plasmids | colonies | flat | intermediate | transformed |
|---|---|---|---|---|
| pMNC[1] | 100 ± 0% | 0 ± 0% | 0 ± 1% | 100 ± 1% |
| pMNC301-2[2] | 61 ± 8% | 2 ± 1% | 15 ± 7% | 83 ± 7% |
| pMNC301-1[3] | 30 ± 7% | 15 ± 3% | 15 ± 5% | 70 ± 6% | b) NIH/3T3 co-transfectin with v-Ha-ras (pSV2neo/ras) and p301
   Morphology of neo' colonies

| Plasmids (ratio 1:1) | inhibition[4] | flat | intermediate | transformed |
|---|---|---|---|---|
| ras + pMNC[1] | 0 ± 3% | 27 ± 3% | 17 ± 5% | 56 ± 3% |
| ras + p301-2[2] | 53 ± 4% | 28 ± 1% | 46 ± 9% | 26 ± 7% |
| ras + p301-1[3] | 61 ± 3% | 46 ± 4% | 32 ± 7% | 22 ± 4% |

| Plasmids (ratio 1:4) | | | | |
|---|---|---|---|---|
| ras + pMNC[1] | 0 ± 1% | 33 ± 4% | 23 ± 3% | 44 ± 3% |
| ras + p301-2[2] | 61 ± 5% | 48 ± 5% | 35 ± 7% | 17 ± 4% |
| ras + p301-1[3] | 84 ± 4% | 67 ± 4% | 25 ± 6% | 7 ± 3% |

Cells were transfected and G418-resistant (400 μg ml$^{-1}$) colonies were morphologically examined according to the criteria described in FIG. 2. Percentages are calculated for two experiments with ≧200 (a) or ≧400 (b) colonies per transfection.
[1]vector control
[2]antisense orientation
[3]sense orientation
[4]The efficiency of inhibition or ras transformation is given as percentage reduction in the number of transformed colonies.

Example 2

Association and Kinase Activity of Raf-1 with the EGF Receptor

To determine whether EGF induces the shift in migration in SDS gels that is typical for phosphorylation activation of Raf-1 protein kinase, lysates of treated and control cells were subjected to immunoprecipitation and immunoblotting with Raf-1-specific antiserum. NIH 3T3 cells lacking endogenous EGF-R but expressing approximately 3×10$^5$ human wild-type (HER14) EGF-R or kinase-negative mutant K721A EGF-R were transferred to starvation medium (0.05% calf serum) at early confluency and stimulated with EGF at 40 nM for 0 to 10 min. The effect of EGF on Raf-1 mobility is shown in FIG. 4. In the absence of EGF treatment, Raf-1 migrates as a single polypetide of 72 kDa, corresponding to the expected molecular mass of Raf-1 protein kinase (Bonner, T. I., et al. (1986) *Nucleic Acids Res.* 14:1009–1015). The addition of EFG to HER14 but not to K721A cells resulted in a small increase in apparent mass of Raf-1 to 74 kDa. This shift first became detectable by 5 min, when approximately 50% of Raf-1 protein was affected, and continued to spread so that by 10 min the entire pool of Raf-1 protein had been modified. The inability of EFG to induce the Raf mobility shift in NIH 3T3 cells expressing the kinase-negative mutant of EGF-R demonstrates that receptor dimerization is not sufficient for Raf-1 modification, since the point mutation in K721A does not affect this event (Ulrich, A., et al. (1990) *Cell* 61:203–212). It therefore seemed likely that the kinase activity of the EGF-R was important in mediating induction of the mobility shift in Raf-1.

The increase in apparent molecular mass of Raf-1 protein upon EGF treatment was due to phosphorylation, since incubation with potato acid phosphatase completely reversed the gels retardation. To evaluate the effect of EGF-stimulated raf-1 protein phosphorylation on its serine- and threonine-specific protein kinase-activity, immune complex kinase assays were performed that utilized a synthetic peptide (IVQQFGFQRRASDDGKLTD) (SEQ ID NO: 1) or histone H1 as a substrate. The peptide corresponds to a potential autophosphorylation site in the Raf-1 kinase, which has been altered by substitution of phenylalanine for tyrosine in position 7 so as to restrict it from tyrosine phosphorylation.

For kinase assays, lysates of HER14 and K721A cells were prepared before and after stimulation with 40 nM EGF for 10 min. Comparison of the levels of kinase activity in Raf-containing immunoprecipitates showed a sixfold stimulation in HER14 cells upon EFG treatment (FIG. 5). Similar data were obtained while histone H1 was used as a substrate. Consistent with the absence of the EGF-induced mobility shift of Raf-1 in NIH 3T3 cells expressing the kinase-negative mutant for of the EGF-R, no stimulation of Raf-1 protein kinase activity was observed in K721A cells (FIG. 5). When Raf-1 kinase activity was assayed with a modified version of the substrate peptide in which Ser-12 was replaced by alanine and Tyr-5 was retained, no counts were detected on the spotted filters. This indicates that the kinase activity measured by the assay did not include a contribution of a contaminating tyrosine kinase activity.

Activity EGF-R associates with the candidate signal transducing enzyme PLC$_\gamma$ (Margolis, B., at al. (1990) Mol. Cell. Biol. 10:435–441; Margolis, B., et al. (1989) Cell 57:1101–1107; Meisenhelder, J., et al. (1989) Cell 57:1109–1112; Wahl, M., et al. (1989) Proc. Natl. Acad. Sci. USA 86:1568–1572). Similarly, Raf-1 was shown to coimmunoprecipitate with activated PDGF-β receptor in cell lines expressing high levels of receptors (Morrison, D. K., et al. (1989) Cell 58:648–657). To evaluate whether ligand-induced activation of Raf-1 protein kinase by the EGF-R correlated with receptor association, two cell systems were used: the NIH 3T3 cells expressing wild-type and mutant receptors (FIG. 6A) and human A431 cells (FIG. 6B) expressing approximately 2×10$^6$ EGF-R per cell (15, 16). Serum-starved cells were stimulated with 40 nM EGF for 10 min. and lysates from cells were immunoprecipitated with Raf-1 or EGF-R specific antibodies. After separation by SDS-PAGE and transfer to nitrocellulose, immunoblotting was performed with either anti-EGF-R or anti-Raf-1 antibodies. EGF-R is present in anti-Raf-1 antibody immunoprecipitates from EGF-treated cells (FIG. 6). The coprecipitating EGF-R in HER14 cells has a decreased mobility on PAGE, compared with that of the EGF-R from untreated controls (FIG. 6A, lanes 4 and 6); this decreased mobility was previously demonstrated to be due to ligand-induced autophosphorylation (Margolis, B., et al. (1989) Cell 57:1101–1107). Cells expressing the kinase-negative mutant receptor KD712A did not show the mobility shift in the EGF-R upon EGF treatment and lacked EGF stimulation of EGF-R Raf-1 coimmunoprecipitation. A small amount of unshifted EGF-R was detected in Raf-1 immunoprecipitates from all cells; this EGF-R could be reduced by preclearing vith preimmune serum. EGF-R can be coprecipitated in lysates from EGF-treated A431 cells, whereas there is not EGF-R present in immunoprecipitates from untreated cells (FIG. 6). sequential reprobing of the Western blot with polyclonal Raf-1 rabbit antiserum (FIG. 6B) indicates that a small fraction (~1%) of the EGF-R associates with shifted Raf-1. Furthermore, the blot demonstrates that the EGF-R-Raf-1 association was not due to unequal loading of the gel with Raf-1 immunoprecipitates. Estimates from three independent experiments indicate that the fraction of immunoprecipitable EGF-R protein that is present in Raf-1 antibody precipitates from EGF-treated HER14 or A431 cells is on the order of 1.0%.

Considering the observed association of Raf-1 protein with activated EGF-R as well as the EGF-induced mobility shift of Raf-1, it might be expected that the receptor-associated fraction of Raf-1 was phosphorylated on tyrosine. The immunoblots from experiments in FIG. 6 were therefore reprobed with antiphosphotyrosine antibodies. The antibodies readily detected EGF-induced tyrosine phosphorylation of the EGF-R, PLCτ, GAP, and other unknown substrates (Ulrich, A., et al. (1990) Cell 61:203–212), but no tyrosine phosphorylated bands in the size range of Raf-1 protein were detected. The experiment was scaled up to examine the presence of tyrosine-phosphorylated Raf-1 protein in anti-Raf or anti-EGF-R antibody immunoprecipiates from $10^8$ HER14 cells per lane; again, tyrosine phosphorylation of Raf-1 could not be detected. Consistent with the absence of anti-phosphotyrosine antibody-reactive Raf-1 protein, phosphoamino acid analysis of Raf-1 from EGF-treated cells did not reveal any phosphotyrosine (FIG. 7). For this experiment, $10^7$ HER14 cells were labeled with $^{32}$Pi, and the Raf-1 proteins were immunoprecipitated with anti-v-Raf 30-kDa polyclonal antiserum and subjected to SDS-PAGE. Phospholabeled Raf-1 protein was excised from the gel, electroeluted, and hydrolyzed in 6 N HCl. The only labeled phosphoamino acid detectable was phosphoserinel thus it can be concluded that EGF induced an increase in serine phosphorylation of c-Raf (FIG. 7). When the same experiment was done with A431 cells, trace amounts of phosphotyrosine were detected that were independent of EGF treatment. The lower limit for detection of phosphotyrosine in Raf-1 in these experiments was on the order of 1% of phosphoserine.

The absence of tyrosine phosphorylation of Raf-1 protein in response to EGF in HER14 cells raises the possibility that serine protein kinase(s) acts as an intermediate in a kinase cascade connecting the stimulated EGF-R to activation of Raf-1 kinase. One candidate for this role is PKC, since this enzyme has previously been shown, upon treatment of cells with tetradecanoylphorbol-13-acetate (TPA), to trigger Raf-1 phosphorylation and kinase activation (Morrison, D. K., et al. (1988) Proc. Natl. Acad. Sci. USA 85:8855–8859; Siegel, J. N., et al. (1990) J. Biol. Chem. 265:18472–18480). It was therefore examined whether EGF induction of the Raf-1 mobility shift was dependent on the presence of PKC (FIG. 8). HER14 cells were pretreated with 200 ng of TPA for 72 h for complete downregulation of PKC and then tested for their ability to respond to EGF with Raf-1 retardation. The PKC down-regulation by pretreatment with TPA was effective in eliminating the TPA-induced Raf-1 retardation. In contrast, EGF-induced Raf-1 mobility shift was not blocked by down-regulation of PKC.

All publications mentioned hereinabove are hereby incorporated in their entirety by reference. In particular, Kolch W et al (1991) Nature 349:426–428 and App H et al (1991) Molecular and Cellular Biology 11(2):913–919 are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of inhibiting a cellular transformation phenotype induced by an oncogene, wherein the protein encoded by the oncogene functions upstream of a raf gene product in a ras-dependent signal transduction pathway, comprising inhibiting the formation of an active Raf protein kinase in a cultured cell containing said upstream oncogene so as to inhibit the expression of said cellular transformation phenotype of said upstream oncogene.

2. The method of claim 1, wherein said cellular transformation phenotype is inhibited by a nucleic acid antisense to raf.

3. The method of claim 1, wherein said cellular transformation phenotype is induced by a ras oncogene product.

4. The method of claim 1, wherein said Raf protein kinase is C-raf.

5. A method of testing for inhibitors of a cellular transformation phenotype induced by an oncogene, wherein the protein encoded by the oncogene functions upstream of a Raf protein kinase in a ras-dependent signal transduction pathway, comprising introducing said inhibitor into a cultured cell expressing said Raf protein kinase and determining the effect of said inhibitor on the expression of said Raf protein kinase, the inhibition of the expression of said Raf protein kinase indicating said inhibitor has the ability to inhibit said cellular transformation phenotype.

6. The method of claim 5, wherein said cellular transformation phenotype is induced by a ras oncogene product.

7. The method of claim 5, wherein said Raf protein kinase is C-raf.

8. A method of inhibiting a cellular transformation phenotype induced by an oncogene, wherein the protein encoded by the oncogene functions upstream of a raf gene product in a ras-dependent signal transduction pathway, comprising inhibiting an active Raf protein kinase in a cultured cell containing said upstream oncogene so as to inhibit the expression of said cellular transformation phenotype of said upstream oncogene.

9. The method of claim 8, wherein said active Raf protein kinase is inhibited by a kinase-defective Raf-1.

10. The method of claim 8, wherein said active Raf protein kinase is inhibited by a truncate, kinase-defective Raf-1.

11. The method of claim 8, wherein said cellular transformation phenotype is induced by a ras oncogene product.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 19 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Ile Val Gln Gln Phe Gly Phe Gln Arg Arg Ala Ser Asp Asp Gly Leu
1               5                   10                  15

Lys Thr Asp (2) INFORMATION FOR SEQ ID NO:2:

(i) SEQUENCE CHARACTERISTICS:
      (A) LENGTH: 2975 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
CCGAATGTGA CCGCCTCCGC TCCCTACCCG CCGCGGGGAG GAGGAGCGGG CGAGAACGTG      60
CCGCCGAACG ACAGGACGTT GGGGCGGCCT GGCTCCCTCA GGTTTAAGAA TTGTTTAAGC     120
TGCATCAATG GAGCACATAC AGGGAGCTTG GAAGACGATC AGCAATGGTT TTGGATTCAA     180
AGATGCCGTG TTTGATGGCT CCAGCTGCAT CTCTCCTACA ATAGTTCAGC AGTTTGGCTA     240
TCAGCGCCGG GCATCAGATG ATGGCAAACT CACAGATCCT TCTAAGACAA GCAACACTAT     300
CCGTGTTTTC TTGCCGAACA AGCAAAGAAC AGTGGTCAAT GTGCGAAATG GAATGAGCTT     360
GCATGACTGC CTTATGAAAG CACTCAAGGT GAGGGGCCTG CAACCAGAGT GCTGTGCAGT     420
GTTCAGACTT CTCCACGAAC ACAAAGGTAA AAAAGCACGC TTAGATTGGA ATACTGATGC     480
TGCGTCTTTG ATTGGAGAAG AACTTCAAGT AGATTTCCTG GATCATGTTC CCCTCACAAC     540
ACACAACTTT GCTCGGAAGA CGTTCCTGAA GCTTGCCTTC TGTGACATCT GTCAGAAATT     600
CCTGCTCAAT GGATTTCGAT GTCAGACTTG TGGCTACAAA TTTCATGAGC ACTGTAGCAC     660
CAAAGTACCT ACTATGTGTG TGGACTGGAG TAACATCAGA CAACTCTTAT TGTTTCCAAA     720
TTCCACTATT GGTGATAGTG GAGTCCCAGC ACTACCTTCT TTGACTATGC GTCGTATGCG     780
AGAGTCTGTT TCCAGGATGC CTGTTAGTTC TCAGCACAGA TATTCTACAC CTCACGCCTT     840
CACCTTTAAC ACCTCCAGTC CCTCATCTGA AGGTTCCCTC TCCCAGAGGC AGAGGTCGAC     900
ATCCACACCT AATGTCCACA TGGTCAGCAC CACGCTGCCT GTGGACAGCA GGATGATTGA     960
GGATGCAATT CGAAGTCACA GCGAATCAGC CTCACCTTCA GCCCTGTCCA GTAGCCCCAA    1020
CAATCTGAGC CCAACAGGCT GGTCACAGCC GAAAACCCCC GTGCCAGCAC AAAGAGAGCG    1080
GGCACCAGTA TCTGGGACCC AGGAGAAAAA CAAAATTAGG CCTCGTGGAC AGAGAGATTC    1140
AAGCTATTAT TGGAAATAG AAGCCAGTGA AGTGATGCTG TCCACTCGGA TTGGGTCAGG    1200
CTCTTTTGGA ACTGTTTATA AGGGTAAATG GCACGGAGAT GTTGCAGTAA AGATCCTAAA    1260
GGTTGTCGAC CCAACCCCAG AGCAATTCCA GGCCTTCAGG AATGAGGTGG CTGTTCTGCG    1320
CAAAACACGG CATGTGAACA TTCTGCTTTT CATGGGGTAC ATGACAAAGG ACAACCTGGC    1380
AATTGTGACC CAGTGGTGCG AGGGCAGCAG CCTCTACAAA CACCTGCATG TCCAGGAGAC    1440
CAAGTTTCAG ATGTTCCAGC TAATTGACAT TGCCCGGCAG ACGGCTCAGG GAATGGACTA    1500
TTTGCATGCA AAGAACATCA TCCATAGAGA CATGAAATCC AACAATATAT TTCTCCATGA    1560
AGGCTTAACA GTGAAAATTG GAGATTTTGG TTTGGCAACA GTAAAGTCAC GCTGGAGTGG    1620
TTCTCAGCAG GTTGAACAAC CTACTGGCTC TGTCCTCTGG ATGGCCCAG AGGTGATCCG    1680
AATGCAGGAT AACAACCCAT TCAGTTTCCA GTCGGATGTC TACTCCTATG GCATCGTATT    1740
GTATGAACTG ATGACGGGGG AGCTTCCTTA TTCTCACATC AACAACCGAG ATCAGATCAT    1800
CTTCATGGTG GGCCGAGGAT ATGCCTCCCC AGATCTTAGT AAGCTATATA AGAACTGCCC    1860
CAAAGCAATG AAGAGGCTGG TAGCTGACTG TGTGAAGAAA GTAAAGGAAG AGAGGCCTCT    1920
TTTTCCCCAG ATCCTGTCTT CCATTGAGCT GCTCCAACAC TCTCTACCGA AGATCAACCG    1980
GAGCGCTTCC GAGCCATCCT TGCATCGGGC AGCCACACT GAGGATATCA ATGCTTGCAC    2040
GCTGACCACG TCCCCGAGGC TGCCTGTCTT CTAGTTGACT TTGCACCTGT CTTCAGGCTG    2100
CCAGGGGAGG AGGAGAAGCC AGCAGGCACC ACTTTTCTGC TCCCTTTCTC CAGAGGCAGA    2160
ACACATGTTT TCAGAGAAGC TCTGCTAAGG ACCTTCTAGA CTGCTCACAG GGCCTTAACT    2220
```

```
TCATGTTGCC TTCTTTTCTA TCCCTTTGGG CCCTGGGAGA AGGAAGCCAT TTGCAGTGCT    2280

GGTGTGTCCT GCTCCCTCCC CACATTCCCC ATGCTCAAGG CCCAGCCTTC TGTAGATGCG    2340

CAAGTGGATG TTGATGGTAG TACAAAAAGC AGGGGCCCAG CCCCAGCTGT TGGCTACATG    2400

AGTATTTAGA GGAAGTAAGG TAGCAGGCAG TCCAGCCCTG ATGTGGAGAC ACATGGGATT    2460

TTGGAAATCA GCTTCTGGAG GAATGCATGT CACAGGCGGG ACTTTCTTCA GAGAGTGGTG    2520

CAGCGCCAGA CATTTTGCAC ATAAGGCACC AAACAGCCCA GGACTGCCGA GACTCTGGCC    2580

GCCCGAAGGA GCCTGCTTTG GTACTATGGA ACTTTTCTTA GGGACACGT CCTCCTTTCA     2640

CAGCTTCTAA GGTGTCCAGT GCATTGGGAT GGTTTTCCAG GCAAGGCACT CGGCCAATCC    2700

GCATCTCAGC CCTCTCAGGA GCAGTCTTCC ATCATGCTGA ATTTTGTCTT CCAGGAGCTG    2760

CCCCTATGGG GCGGGCCGCA GGGCCAGCCT GTTTCTCTAA CAAACAAACA AACAAACAGC    2820

CTTGTTTCTC TAGTCACATC ATGTGTATAC AAGGAAGCCA GGAATACAGG TTTTCTTGAT    2880

GATTTGGGTT TTAATTTTGT TTTTATTGCA CCTGACAAAA TACAGTTATC TGATGGTCCC    2940

TCAATTATGT TATTTTAATA AAATAAATTA AATTT                              2975
```

(2) INFORMATION FOR SEQ ID NO:3:

(i) SEQUENCE CHARACTERISTICS:
        (A) LENGTH: 648 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Glu His Ile Gln Gly Ala Trp Lys Thr Ile Ser Asn Gly Phe Gly
1               5                   10                  15

Phe Lys Asp Ala Val Phe Asp Gly Ser Ser Cys Ile Ser Pro Thr Ile
            20                  25                  30

Val Gln Gln Phe Gly Tyr Gln Arg Arg Ala Ser Asp Asp Gly Lys Leu
        35                  40                  45

Thr Asp Pro Ser Lys Thr Ser Asn Thr Ile Arg Val Phe Leu Pro Asn
    50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
            100                 105                 110

Asp Trp Asn Thr Asp Ala Ala Ser Leu Ile Gly Glu Glu Leu Gln Val
        115                 120                 125

Asp Phe Leu Asp His Val Pro Leu Thr Thr His Asn Phe Ala Arg Lys
    130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Ile Gly Asp Ser Gly Val Pro Ala
        195                 200                 205

Leu Pro Ser Leu Thr Met Arg Arg Met Arg Glu Ser Val Ser Arg Met
```

```
            210                 215                 220
Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ser Thr Pro Asn Val His Met Val Ser Thr Thr Leu Pro Val
                260                 265                 270

Asp Ser Arg Met Ile Glu Asp Ala Ile Arg Ser His Ser Glu Ser Ala
            275                 280                 285

Ser Pro Ser Ala Leu Ser Ser Ser Pro Asn Asn Leu Ser Pro Thr Gly
        290                 295                 300

Trp Ser Gln Pro Lys Thr Pro Val Pro Ala Gln Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
            340                 345                 350

Thr Arg Ile Gly Ser Gly Ser Phe Gly Thr Val Tyr Lys Gly Lys Trp
        355                 360                 365

His Gly Asp Val Ala Val Lys Ile Leu Lys Val Asp Pro Thr Pro
        370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
                420                 425                 430

Leu His Val Gln Glu Thr Lys Phe Gln Met Phe Gln Leu Ile Asp Ile
            435                 440                 445

Ala Arg Gln Thr Ala Gln Gly Met Asp Tyr Leu His Ala Lys Asn Ile
        450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
                485                 490                 495

Ser Gly Ser Gln Gln Val Glu Gln Pro Thr Gly Ser Val Leu Trp Met
                500                 505                 510

Ala Pro Glu Val Ile Arg Met Gln Asp Asn Asn Pro Phe Ser Phe Gln
            515                 520                 525

Ser Asp Val Tyr Ser Tyr Gly Ile Val Leu Tyr Glu Leu Met Thr Gly
        530                 535                 540

Glu Leu Pro Tyr Ser His Ile Asn Asn Arg Asp Gln Ile Ile Phe Met
545                 550                 555                 560

Val Gly Arg Gly Tyr Ala Ser Pro Asp Leu Ser Lys Leu Tyr Lys Asn
                565                 570                 575

Cys Pro Lys Ala Met Lys Arg Leu Val Ala Asp Cys Val Lys Lys Val
                580                 585                 590

Lys Glu Glu Arg Pro Leu Phe Pro Gln Ile Leu Ser Ser Ile Glu Leu
            595                 600                 605

Leu Gln His Ser Leu Pro Lys Ile Asn Arg Ser Ala Ser Glu Pro Ser
        610                 615                 620

Leu His Arg Ala Ala His Thr Glu Asp Ile Asn Ala Cys Thr Leu Thr
625                 630                 635                 640
```

Thr Ser Pro Arg Leu Pro Val Phe
           645

(2) INFORMATION FOR SEQ ID NO:4:

(i) SEQUENCE CHARACTERISTICS:
        (A) LENGTH: 2458 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
TGACCCAATA AGGGTGGAAG GCTGAGTCCC GCAGAGCCAA TAACGAGAGT CCGAGAGGCG      60

ACGGAGGCGG ACTCTGTGAG GAAACAAGAA GAGAGGCCCA AGATGGAGAC GGCGGCGGCT     120

GTAGCGGCGT GACAGGAGCC CCATGGCACC TGCCCAGCCC CACCTCAGCC CATCTTGACA     180

AAATCTAAGG CTCCATGGAG CCACCACGGG GCCCCCCTGC CAATGGGGCC GAGCCATCCC     240

GGGCAGTGGG CACCGTCAAA GTATACCTGC CAACAAGCA ACGCACGGTG GTGACTGTCC      300

GGGATGGCAT GAGTGTCTAC GACTCTCTAG ACAAGGCCCT GAAGGTGCGG GGTCTAAATC     360

AGGACTGCTG TGTGGTCTAC CGACTCATCA AGGGACGAAA GACGGTCACT GCCTGGGACA     420

CAGCCATTGC TCCCCTGGAT GGCGAGGAGC TCATTGTCGA GGTCCTTGAA GATGTCCCGC     480

TGACCATGCA CAATTTTGTA CGGAAGACCT TCTTCAGCCT GGCGTTCTGT GACTTCTGCC     540

TTAAGTTTCT GTTCCATGGC TTCCGTTGCC AAACCTGTGG CTACAAGTTC CACCAGCATT     600

GTTCCTCCAA GGTCCCCACA GTCTGTGTTG ACATGAGTAC CAACCGCCAA CAGTTCTACC     660

ACAGTGTCCA GGATTTGTCC GGAGGCTCCA GACAGCATGA GGCTCCCTCG AACCGCCCCC     720

TGAATGAGTT GCTAACCCCC CAGGGTCCCA GCCCCCGCAC CCAGCACTGT GACCCGGAGC     780

ACTTCCCCTT CCCTGCCCCA GCCAATGCCC CCTACAGCG CATCCGCTCC ACGTCCACTC      840

CCAACGTCCA TATGGTCAGC ACCACGGCCC CCATGGACTC CAACCTCATC CAGCTCACTG     900

GCCAGAGTTT CAGCACTGAT GCTGCCGGTA GTAGAGGAGG TAGTGATGGA ACCCCCCGGG    960

GGAGCCCCAG CCCAGCCAGC GTGTCCTCGG GGAGGAAGTC CCCACATTCC AAGTCACCAG    1020

CAGAGCAGCG CGAGCGGAAG TCCTTGGCCG ATGACAAGAA GAAAGTGAAG AACCTGGGGT    1080

ACCGGGATTC AGGCTATTAC TGGGAGGTAC CACCCAGTGA GGTGCAGCTG CTGAAGAGGA    1140

TCGGGACGGG CTCGTTTGGC ACCGTGTTTC GAGGGCGGTG GCATGGCGAT GTGGCCGTGA    1200

AGGTGCTCAA GGTGTCCCAG CCCACAGCTG AGCAGGCCCA GGCTTTCAAG AATGAGATGC    1260

AGGTGCTCAG GAAGACGCGA CATGTCAACA TCTTGCTGTT TATGGGCTTC ATGACCCGGC    1320

CGGGATTTGC CATCATCACA CAGTGGTGTG AGGGCTCCAG CCTCTACCAT CACCTGCATG    1380

TGGCCGACAC ACGCTTCGAC ATGGTCCAGC TCATCGACGT GGCCCGGCAG ACTGCCCAGG    1440

GCATGGACTA CCTCCATGCC AAGAACATCA TCCACCGAGA TCTCAAGTCT AACAACATCT    1500

TCCTACATGA GGGGCTCACG GTGAAGATCG GTGACTTTGG CTTGGCCACA GTGAAGACTC    1560

GATGGAGCGG GGCCCAGCCC TTGGAGCAGC CCTCAGGATC TGTGCTGTGG ATGGCAGCTG    1620

AGGTGATCCG TATGCAGGAC CCGAACCCCT ACAGCTTCCA GTCAGACGTC TATGCCTACG    1680

GGGTTGTGCT CTACGAGCTT ATGACTGGCT CACTGCCTTA CAGCCACATT GGCTGCCGTG    1740

ACCAGATTAT CTTTATGGTG GGCCGTGGCT ATCTGTCCCC GGACCTCAGC AAAATCTCCA    1800

GCAACTGCCC CAAGGCCATG CGGCGCCTGC TGTCTGACTG CCTCAAGTTC CAGCGGGAGG    1860
```

```
AGCGGCCCCT CTTCCCCCAG ATCCTGGCCA CAATTGAGCT GCTGCAACGG TCACTCCCCA      1920

AGATTGAGCG GAGTGCCTCG GAACCCTCCT TGCACCGCAC CCAGGCCGAT GAGTTGCCTG      1980

CCTGCCTACT CAGCGCAGCC CGCCTTGTGC CTTAGGCCCC GCCCAAGCCA CCAGGGAGCC      2040

AATCTCAGCC CTCCACGCCA AGGAGCCTTG CCCACCAGCC AATCAATGTT CGTCTCTGCC      2100

CTGATGCTGC CTCAGGATCC CCCATTCCCC ACCCTGGGAG ATGAGGGGGT CCCCATGTGC      2160

TTTTCCAGTT CTTCTGGAAT TGGGGACCC CCGCCAAAGA CTGAGCCCCC TGTCTCCTCC       2220

ATCATTTGGT TTCCTCTTGG CTTTGGGGAT ACTTCTAAAT TTTGGGAGCT CCTCCATCTC      2280

CAATGGCTGG GATTTGTGGC AGGGATTCCA CTCAGAACCT CTCTGGAATT TGTGCCTGAT      2340

GTGCCTTCCA CTGGATTTTG GGGTTCCCAG CACCCCATGT GGATTTTGGG GGGTCCCTTT      2400

TGTGTCTCCC CCGCCATTCA AGGACTCCTC TCTTTCTTCA CCAAGAAGCA CAGAATTC       2458
```

(2) INFORMATION FOR SEQ ID NO:5:

(i) SEQUENCE CHARACTERISTICS:
        (A) LENGTH: 606 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Met Glu Pro Pro Arg Gly Pro Pro Ala Asn Gly Ala Glu Pro Ser Arg
1               5                   10                  15

Ala Val Gly Thr Val Lys Val Tyr Leu Pro Asn Lys Gln Arg Thr Val
            20                  25                  30

Val Thr Val Arg Asp Gly Met Ser Val Tyr Asp Ser Leu Asp Lys Ala
        35                  40                  45

Leu Lys Val Arg Gly Leu Asn Gln Asp Cys Cys Val Val Tyr Arg Leu
    50                  55                  60

Ile Lys Gly Arg Lys Thr Val Thr Ala Trp Asp Thr Ala Ile Ala Pro
65                  70                  75                  80

Leu Asp Gly Glu Glu Leu Ile Val Glu Val Leu Glu Asp Val Pro Leu
                85                  90                  95

Thr Met His Asn Phe Val Arg Lys Thr Phe Phe Ser Leu Ala Phe Cys
            100                 105                 110

Asp Phe Cys Leu Lys Phe Leu Phe His Gly Phe Arg Cys Gln Thr Cys
        115                 120                 125

Gly Tyr Lys Phe His Gln His Cys Ser Ser Lys Val Pro Thr Val Cys
    130                 135                 140

Val Asp Met Ser Thr Asn Arg Gln Gln Phe Tyr His Ser Val Gln Asp
145                 150                 155                 160

Leu Ser Gly Gly Ser Arg Gln His Glu Ala Pro Ser Asn Arg Pro Leu
                165                 170                 175

Asn Glu Leu Leu Thr Pro Gln Gly Pro Ser Pro Arg Thr Gln His Cys
            180                 185                 190

Asp Pro Glu His Phe Pro Phe Pro Ala Pro Ala Asn Ala Pro Leu Gln
        195                 200                 205

Arg Ile Arg Ser Thr Ser Thr Pro Asn Val His Met Val Ser Thr Thr
    210                 215                 220

Ala Pro Met Asp Ser Asn Leu Ile Gln Leu Thr Gly Gln Ser Phe Ser
225                 230                 235                 240

Thr Asp Ala Ala Gly Ser Arg Gly Gly Ser Asp Gly Thr Pro Arg Gly
```

```
                        245                 250                 255
Ser Pro Ser Pro Ala Ser Val Ser Ser Gly Arg Lys Ser Pro His Ser
                260                 265                 270
Lys Ser Pro Ala Glu Gln Arg Glu Arg Lys Ser Leu Ala Asp Asp Lys
            275                 280                 285
Lys Lys Val Lys Asn Leu Gly Tyr Arg Asp Ser Gly Tyr Tyr Trp Glu
        290                 295                 300
Val Pro Pro Ser Glu Val Gln Leu Leu Lys Arg Ile Gly Thr Gly Ser
305                 310                 315                 320
Phe Gly Thr Val Phe Arg Gly Arg Trp His Gly Asp Val Ala Val Lys
                325                 330                 335
Val Leu Lys Val Ser Gln Pro Thr Ala Glu Gln Ala Gln Ala Phe Lys
            340                 345                 350
Asn Glu Met Gln Val Leu Arg Lys Thr Arg His Val Asn Ile Leu Leu
        355                 360                 365
Phe Met Gly Phe Met Thr Arg Pro Gly Phe Ala Ile Ile Thr Gln Trp
    370                 375                 380
Cys Glu Gly Ser Ser Leu Tyr His His Leu His Val Ala Asp Thr Arg
385                 390                 395                 400
Phe Asp Met Val Gln Leu Ile Asp Val Ala Arg Gln Thr Ala Gln Gly
                405                 410                 415
Met Asp Tyr Leu His Ala Lys Asn Ile Ile His Arg Asp Leu Lys Ser
            420                 425                 430
Asn Asn Ile Phe Leu His Glu Gly Leu Thr Val Lys Ile Gly Asp Phe
        435                 440                 445
Gly Leu Ala Thr Val Lys Thr Arg Trp Ser Gly Ala Gln Pro Leu Glu
    450                 455                 460
Gln Pro Ser Gly Ser Val Leu Trp Met Ala Ala Glu Val Ile Arg Met
465                 470                 475                 480
Gln Asp Pro Asn Pro Tyr Ser Phe Gln Ser Asp Val Tyr Ala Tyr Gly
                485                 490                 495
Val Val Leu Tyr Glu Leu Met Thr Gly Ser Leu Pro Tyr Ser His Ile
            500                 505                 510
Gly Cys Arg Asp Gln Ile Ile Phe Met Val Gly Arg Gly Tyr Leu Ser
        515                 520                 525
Pro Asp Leu Ser Lys Ile Ser Ser Asn Cys Pro Lys Ala Met Arg Arg
    530                 535                 540
Leu Leu Ser Asp Cys Leu Lys Phe Gln Arg Glu Glu Arg Pro Leu Phe
545                 550                 555                 560
Pro Gln Ile Leu Ala Thr Ile Glu Leu Leu Gln Arg Ser Leu Pro Lys
                565                 570                 575
Ile Glu Arg Ser Ala Ser Glu Pro Ser Leu His Arg Thr Gln Ala Asp
            580                 585                 590
Glu Leu Pro Ala Cys Leu Leu Ser Ala Ala Arg Leu Val Pro
        595                 600                 605

(2) INFORMATION FOR SEQ ID NO:6:

(i) SEQUENCE CHARACTERISTICS:
        (A) LENGTH: 2229 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:6:

```
GGGCAATATA TCTGGAGGCC TATGAAGAAT ACACCAGCAA GCTAGATGCA CTCCAACAAA        60

GAGAACAACA GTTATTGGAA TCTCTGGGGA ACGGAACTGA TTTTTCTGTT TCTAGCTCTG       120

CATCAATGGA TACCGTTACA TCTTCTTCCT CTTCTAGCCT TTCAGTGCTA CCTTCATCTC       180

TTTCAGTTTT TCAAAATCCC ACAGATGTGG CACGGAGCAA CCCCAAGTCA CCACAAAAAC       240

CTATCGTTAG AGTCTTCCTG CCCAACAAAC AGAGGACAGT GGTACCTGCA AGGTGTGGAG       300

TTACAGTCCG AGACAGTCTA AAGAAAGCAC TGATGATGAG AGGTCTAATC CCAGAGTGCT       360

GTGCTGTTTA CAGAATTCAG GATGGAGAGA AGAAACCAAT TGGTTGGGAC ACTGATATTT       420

CCTGGCTTAC TGGAGAAGAA TTGCATGTGG AAGTGTTGGA GAATGTTCCA CTTACAACAC       480

ACAACTTTGT ACGAAAAACG TTTTTCACCT TAGCATTTTG TGACTTTTGT CGAAAGCTGC       540

TTTTCCAGGG TTTTCCGCTGT CAAACATGTG GTTATAAATT TCACCAGCGT TGTAGTACAG       600

AAGTTCCACT GATGTGTGTT AATTATGACC AACTTGATTT GCTGTTTGTC TCCAAGTTCT       660

TTGAACACCA CCCAATACCA CAGGAAGAGG CGTCCTTAGC AGAGACTGCC CTAACATCTG       720

GATCATCCCC TTCCGCACCC GCCTCGGACT CTATTGGGCC CCAAATTCTC ACCAGTCCGT       780

CTCCTTCAAA ATCCATTCCA ATTCCACAGC CCTTCCGACC AGCAGATGAA GATCATCGAA       840

ATCAATTTGG GCAACGAGAC CGATCCTCAT CAGCTCCCAA TGTGCATATA AACACAATAG       900

AACCTGTCAA TATTGATGAC TTGATTAGAG ACCAAGGATT TCGTGGTGAT GGAGGATCAA       960

CCACAGGTTT GTCTGCTACC CCCCCTGCCT CATTACCTGG CTCACTAACT AACGTGAAAG      1020

CCTTACAGAA ATCTCCAGGA CCTCAGCGAG AAAGGAAGTC ATCTTCATCC TCAGAAGACA      1080

GGAATCGAAT GAAAACACTT GGTAGACGGG ACTCGAGTGA TGATTGGGAG ATTCCTGATG      1140

GGCAGATTAC AGTGGGACAA AGAATTGGAT CTGGATCATT TGGAACAGTC TACAAGGGAA      1200

AGTGGCATGG TGATGTGGCA GTGAAAATGT TGAATGTGAC AGCACCTACA CCTCAGCAGT      1260

TACAAGCCTT CAAAAATGAA GTAGGAGTAC TCAGGAAAAC ACGACATGTG AATATCCTAC      1320

TCTTCATGGG CTATTCCACA AAGCCACAAC TGGCTATTGT TACCCAGTGG TGTGAGGGCT      1380

CCAGCTTGTA TCACCATCTC CATATCATTG AGACCAAATT TGAGATGATC AAACTTATAG      1440

ATATTGCACG ACAGACTGCA CAGGGCATGG ATTACTTACA CGCCAAGTCA ATCATCCACA      1500

GAGACCTCAA GAGTAATAAT ATATTTCTTC ATGAAGACCT CACAGTAAAA ATAGGTGATT      1560

TTGGTCTAGC TACAGTGAAA TCTCGATGGA GTGGGTCCCA TCAGTTTGAA CAGTTGTCTG      1620

GATCCATTTT GTGGATGGCA CCAGAAGTCA TCAGAATGCA AGATAAAAAT CCATACAGCT      1680

TTCAGTCAGA TGTATATGCA TTTGGAATTG TTCTGTATGA ATTGATGACT GGACAGTTAC      1740

CTTATTCAAA CATCAACAAC AGGGACCAGA TAATTTTTAT GGTGGGACGA GGATACCTGT      1800

CTCCAGATCT CAGTAAGGTA CGGAGTAACT GTCCAAAAGC CATGAAGAGA TTAATGGCAG      1860

AGTGCCTCAA AAAGAAAAGA GATGAGAGAC CACTCTTTCC CCAAATTCTC GCCTCTATTG      1920

AGCTGCTGGC CCGCTCATTG CCAAAAATTC ACCGCAGTGC ATCAGAACCC TCCTTGAATC      1980

GGGCTGGTTT CCAAACAGAG GATTTTAGTC TATATGCTTG TGCTTCTCCA AAAACACCCA      2040

TCCAGGCAGG GGGATATGGT GCGTTTCCTG TCCACTGAAA CAAATGAGTG AGAGAGTTCA      2100

GGAGAGTAGC AACAAAAGGA AAATAAATGA ACATATGTTT GCTTATATGT TAAATTGAAT      2160

AAAATACTCT CTTTTTTTTT AAGGTGGAAA AAAAAAAAA AAAAAAAAA AAAAAAAAA        2220

AAAAAACCC                                                            2229
```

(2) INFORMATION FOR SEQ ID NO:7:

(i) SEQUENCE CHARACTERISTICS:
        (A) LENGTH: 650 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Met Asp Thr Val Thr Ser Ser Ser Ser Ser Leu Ser Val Leu Pro
 1               5                  10                  15

Ser Ser Leu Ser Val Phe Gln Asn Pro Thr Asp Val Ala Arg Ser Asn
            20                  25                  30

Pro Lys Ser Pro Gln Lys Pro Ile Val Arg Val Phe Leu Pro Asn Lys
            35                  40                  45

Gln Arg Thr Val Val Pro Ala Arg Cys Gly Val Thr Val Arg Asp Ser
 50                      55                  60

Leu Lys Lys Ala Leu Met Met Arg Gly Leu Ile Pro Glu Cys Cys Ala
 65                  70                  75                  80

Val Tyr Arg Ile Gln Asp Gly Glu Lys Lys Pro Ile Gly Trp Asp Thr
                 85                  90                  95

Asp Ile Ser Trp Leu Thr Gly Glu Glu Leu His Val Glu Val Leu Glu
                100                 105                 110

Asn Val Pro Leu Thr Thr His Asn Phe Val Arg Lys Thr Phe Phe Thr
            115                 120                 125

Leu Ala Phe Cys Asp Phe Cys Arg Lys Leu Leu Phe Gln Gly Phe Arg
130                 135                 140

Cys Gln Thr Cys Gly Tyr Lys Phe His Gln Arg Cys Ser Thr Glu Val
145                 150                 155                 160

Pro Leu Met Cys Val Asn Tyr Asp Gln Leu Asp Leu Leu Phe Val Ser
                165                 170                 175

Lys Phe Phe Glu His His Pro Ile Pro Gln Glu Glu Ala Ser Leu Ala
            180                 185                 190

Glu Thr Ala Leu Thr Ser Gly Ser Ser Pro Ser Ala Pro Ala Ser Asp
            195                 200                 205

Ser Ile Gly Pro Gln Ile Leu Thr Ser Pro Ser Pro Ser Lys Ser Ile
            210                 215                 220

Pro Ile Pro Gln Pro Phe Arg Pro Ala Asp Glu Asp His Arg Asn Gln
225                 230                 235                 240

Phe Gly Gln Arg Asp Arg Ser Ser Ala Pro Asn Val His Ile Asn
                245                 250                 255

Thr Ile Glu Pro Val Asn Ile Asp Asp Leu Ile Arg Asp Gln Gly Phe
                260                 265                 270

Arg Gly Asp Gly Gly Ser Thr Thr Gly Leu Ser Ala Thr Pro Pro Ala
            275                 280                 285

Ser Leu Pro Gly Ser Leu Thr Asn Val Lys Ala Leu Gln Lys Ser Pro
            290                 295                 300

Gly Pro Gln Arg Glu Arg Lys Ser Ser Ser Ser Glu Asp Arg Asn
305                 310                 315                 320

Arg Met Lys Thr Leu Gly Arg Arg Asp Ser Ser Asp Asp Trp Glu Ile
                325                 330                 335

Pro Asp Gly Gln Ile Thr Val Gly Gln Arg Ile Gly Ser Gly Ser Phe
            340                 345                 350

Gly Thr Val Tyr Lys Gly Lys Trp His Gly Asp Val Ala Val Lys Met
```

```
                355                 360                 365
Leu Asn Val Thr Ala Pro Thr Pro Gln Gln Leu Gln Ala Phe Lys Asn
    370                 375                 380
Glu Val Gly Val Leu Arg Lys Thr Arg His Val Asn Ile Leu Leu Phe
385                 390                 395                 400
Met Gly Tyr Ser Thr Lys Pro Gln Leu Ala Ile Val Thr Gln Trp Cys
                405                 410                 415
Glu Gly Ser Ser Leu Tyr His His Leu His Ile Ile Glu Thr Lys Phe
                420                 425                 430
Glu Met Ile Lys Leu Ile Asp Ile Ala Arg Gln Thr Ala Gln Gly Met
                435                 440                 445
Asp Tyr Leu His Ala Lys Ser Ile Ile His Arg Asp Leu Lys Ser Asn
450                 455                 460
Asn Ile Phe Leu His Glu Asp Leu Thr Val Lys Ile Gly Asp Phe Gly
465                 470                 475                 480
Leu Ala Thr Val Lys Ser Arg Trp Ser Gly Ser His Gln Phe Glu Gln
                485                 490                 495
Leu Ser Gly Ser Ile Leu Trp Met Ala Pro Glu Val Ile Arg Met Gln
                500                 505                 510
Asp Lys Asn Pro Tyr Ser Phe Gln Ser Asp Val Tyr Ala Phe Gly Ile
                515                 520                 525
Val Leu Tyr Glu Leu Met Thr Gly Gln Leu Pro Tyr Ser Asn Ile Asn
530                 535                 540
Asn Arg Asp Gln Ile Ile Phe Met Val Gly Arg Gly Tyr Leu Ser Pro
545                 550                 555                 560
Asp Leu Ser Lys Val Arg Ser Asn Cys Pro Lys Ala Met Lys Arg Leu
                565                 570                 575
Met Ala Glu Cys Leu Lys Lys Lys Arg Asp Glu Arg Pro Leu Phe Pro
                580                 585                 590
Gln Ile Leu Ala Ser Ile Glu Leu Leu Ala Arg Ser Leu Pro Lys Ile
                595                 600                 605
His Arg Ser Ala Ser Glu Pro Ser Leu Asn Arg Ala Gly Phe Gln Thr
610                 615                 620
Glu Asp Phe Ser Leu Tyr Ala Cys Ala Ser Pro Lys Thr Pro Ile Gln
625                 630                 635                 640
Ala Gly Gly Tyr Gly Ala Phe Pro Val His
                645                 650

(2) INFORMATION FOR SEQ ID NO:8:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AAATACAGTT ATCTGATGGT CCCTCAATTA TGTTATTTTA ATAAAATAAA TTAAATTTAG       60

GTGTAATGGC TGGCTGTTAC CTCCTTTTAA AGTAATTCTG AGCTCACAAC TTGAATGCCC      120

CATTTGTTCA CCCTCTTCAG GATCAGAATT C                                      151
```